(12) United States Patent
Ruoslahti et al.

(10) Patent No.: US 8,536,132 B2
(45) Date of Patent: Sep. 17, 2013

(54) LYMPHATIC ZIP CODES IN TUMORS AND PRE-MALIGNANT LESIONS

(75) Inventors: Erkki Ruoslahti, Buellton, CA (US); Lianglin Zhang, San Diego, CA (US); Douglas Hanahan, San Francisco, CA (US)

(73) Assignees: Sanford-Burnham Medical Research Institute, La Jolla, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 13/024,445

(22) Filed: Feb. 10, 2011

(65) Prior Publication Data

US 2011/0212162 A1    Sep. 1, 2011

Related U.S. Application Data

(62) Division of application No. 11/670,318, filed on Feb. 1, 2007, now Pat. No. 7,919,466.

(60) Provisional application No. 60/764,175, filed on Feb. 1, 2006.

(51) Int. Cl.
*A61K 38/00* (2006.01)
*A61P 35/00* (2006.01)

(52) U.S. Cl.
USPC .................. 514/19.2; 514/19.3; 514/19.5

(58) Field of Classification Search
None
See application file for complete search history.

(56) References Cited

FOREIGN PATENT DOCUMENTS

| WO | WO 99/50461 | 10/1999 |
|---|---|---|
| WO | WO 02/086113 | 10/2002 |
| WO | WO 03/040693 | 5/2003 |
| WO | WO 2005/039495 | 5/2005 |
| WO | WO 2007/090194 | 8/2007 |

OTHER PUBLICATIONS

Alitalo, et al, "Lymphangiogenesis and cancer: meeting report", *Can Res*, 64:9225-29 (2004).
Arap,et al., "Chemotherapy targeted to tumor vasculature", *Curr Opin Oncol*, 10:560-5 (1998).
Arbeit, et al., "Chronic estrogen-induced cervical and vaginal squamous carcinogenesis in human papillomavirus type 16 transgenic mice", *PNAS*, 93:2930-5 (1996).
Arbeit, et al., "Progressive squamous epithelial neoplasia in K14-human papillomavirus type 16 transgenic mice", *J Virol*, 68:4358-68 (1994).
Bae, et al., "Metastatic sublines of an SV40 large T antigen immortalized human prostate epithelial cell line", *Prostate*, 34:275-82 (1998).
Borges, et al., "Platelet-derived growth factor receptor beta and vascular endothelial growth factor receptor 2 bind to the beta 3 integrin through its extracellular domain", *J Biol Chem*, 275: 39867-73 (2000).
Brooks, et al., "Hysterectomy vs. resectoscopic endometrial ablation for the control of abnormal uterine bleeding. A cost-comparative study", *J Reprod Med.*, 39:755-60 (1994).
Cao, et al., "PDGF-BB induces intratumoral lymphangiogenesis and promotes lymphatic metastasis", *Cancer Cell*, 6:333-45 (2004).
Cassella and Skobe, "Lymphatic vessel activation in cancer", *Ann N Y Acad Sci*, 979:120-30 (2002).
Chen, et al., "RGD-Tachyplesin inhibits tumor growth", *Can Res.*, 61(6):2434-8 (2001).
Christian, et al., "Nucleolin expressed at the cell surface is a marker of endothelial cells in angiogenic blood vessels", *J Cell Biol*, 163:871-8 (2003).
Coussens, et al., "Genetic predisposition and parameters of malignant progression in K14-HPV16 transgenic mice", *Am J Pathol*, 149:1899-1917 (1996).
Curnis, et al., "Coupling tumor necrosis factor-alpha with alphaV integrin ligands improves its antineoplastic activity", *Cancer Res*, 64:565-71 (2004).
Curnis, et al., "Enhancement of tumor necrosis factor alpha antitumor imunotherapeutic properties by targeted delivery to aminopeptidase N (CD13)", *Nat Biotech*, 18:1185-90 (2000).
Ellerby, et al., "Anti-cancer activity of targeted pro-apoptotic peptides", *Nat Med*, 5:1032-8 (1999).
Ferrara and Alitalo, "Clinical applications of angiogenic growth factors and their inhibitors",. *Nat Med*, 5:1359-64 (1999).
Guraudo, et al., "An amino-bisphophonate targets MMP-9-expressing macrophages and angiogenesis to impair cervical carcinogenesis", *J Clin Invest.*, 114:623-33 (2004).
Hanahan and Weinberg, "The hallmarks of cancer", *Cell*, 100:57-70 (2000).
Helbig, et al., "NF-kappaB promoted breast cancer cell migration and metastasis by inducing the expression of the chemokine receptor CXCR4", *J Biol Chem*, 278:21631-8 (2003).
Hoffman, et al., "Progressive vascular changes in a transgenic mouse model of squamous cell carcinoma", *Cancer Cell*, 4:383-91 (2003).
Hoffman, et al., "In vivo and ex vivo selections using phage displayed libraries", *Phage Display: A Practical Approach* (Clarkson, T. and Lowman, H., eds.), Oxford University Press, Oxford, U.K (2004).
Hsu, et al., "Longitudinal cohort analysis of lethal prostate cancer progression in transgenic mice", *J Urol*, 160:1500-05 (1998).
Jackson,et al., "LYVE-1, the lymphatic system and tumor lympangiogenesis", *Trends Immunol* ,22:317-21 (2001).
Joyce, et al., "Stage-specific vasculr markers revealed by phage display in a mouse model of pancreatic islet tumorigenesis", *Cancer Cell* , 4:393-403 (2003).
Kang, et al., "Stromal cell derived factor-1: its influence on invasiveness and migration of breast cancer cells in vitro, and its association with prognosis and survival in human breast cancer", *Breast Cancer Res.*, 7:R402-R410 (2005).
Laakkonen, et al., "Antitumor activity of a homing peptide that targets tumor lymphatics and tumor cells", *PNAS*, 101:9381-6 (2004).
Laakkonen, et al., "A tumor-homing peptide with a targeting specificity related to lymphatic vessels", *Nat Med*, 8:751-5 (2002).
Laakkonen, et al., "Peptide targeting of tumor lymph vessels", *Annals of the NY Aca Sci.*, 1131:37-43 (2008).

(Continued)

*Primary Examiner* — Thomas Heard
(74) *Attorney, Agent, or Firm* — Jenkins, Wilson, Taylor & Hunt, P.A.

(57) ABSTRACT

Disclosed herein are compositions and methods for and involving selectively targeting tumor lymphatics.

16 Claims, 9 Drawing Sheets

(56) References Cited

OTHER PUBLICATIONS

Lin, et al., "Inhibition of lymphogenous metastasis using adeno-associated virus-mediated gene transfer of a soluble VEGFR-3 decoy receptor", *Cancer Res*, 65:6901-9 (2005).

Mandriota, et al., "Vascular endothelial growth factor-C-mediated lymphangiogenesis promotes tumour metastasis", *Embo J*, 20:672-82 (2001).

Mouta Carrera, "LYVE-1 is not restricted to the lymph vessels: expression in normal liver blood sinusoids and down-regulation in human liver cancer and cirrhosis", *Cancer Res*, 61:8079-84 (2001).

Nagasawa, et al., "Molecular cloning and structure of a pre-B-cell growth-stimulating factor", *PNAS*, 91:2305-9 (1994).

Padera, et al., "Lymphatic metastasis in the absence of functional intratumor lymphatics", *Science*, 296:1883-6 (2002).

Pasqualini, et al., "Aminopeptidase N is a receptor for tumor-homing peptides and a target for inhibiting angiogenesis", *Cancer Res* 60:722-7 (2000).

Ruoslahti, "Specialization of tumour vasculature", *Nat Rev Cancer*, 2:83-90 (2002).

Ruoslahti, "The RGD story: a personal account", *Matrix Biol* 22, 459-465 (2003).

Saharinen, et al., "Lymphatic vasculature: development, molecular regulation and role in tumor metastasis and inflammation", *Trends Immunol* 25:387-95 (2004).

Skobe, et al., "Induction of tumor lymphangiogenesis by VEGF-C promotes breast cancer metastasis", *Nat Med* 7:192-8 (2001).

Skobe, et al., "Inducton of tumor lymphangiogenesis by VEGF-C promotes beast cancer metastasis", *Nat Med* 7:192-8 (2001).

Stacker, et al., "Lymphangiogenesis and cancer metastasis", *Nat Rev Cancer* 2:573-83 (2002).

Stacker, et al., "VEGF-D promotes the metastatic spread of tumor cells via the lymphatics", *Nat Med*, 7:186-91 (2001).

Tashiro, et al., "Signal sequence trap: a cloning strategy for secreted proteins and type I membrane proteins", *Science*, 261:600-03 (1993).

Valtola, et al., "VEGFR-3 and its ligand VEGF-C are associated with angiogenesis in breast cancer", *Am J Pathol*, 154:1381-90 (1999).

Yao, et al., "Targeting pancreatic islets with phage display assisted by laser pressure catapult microdissection", *Am J Pathol*, 166:625-36 (2005).

Zhang, et al., "Lymphatic zip codes in premalignant lesions and tumors", *Cancer Res.*, 66(11):5696-706 (2006).

```
LSD                         CLSDGKRKC              (SEQ ID NO:1)
hSDF-1   MNAKVVVVLVLVLTALCLSDGKPVS ___ M93         (SEQ ID NO:36)
mSDF-1   MDAKVVAVLALVLAALCLSDGKPVS ___ K89         (SEQ ID NO:37)
         1                17   22
```

LYMPHATIC ZIP CODES IN TUMORS AND PRE-MALIGNANT LESIONS

CROSS-REFERENCE TO RELATED APPLICATIONS

This application is a divisional of U.S. application Ser. No. 11/670,318, filed Feb. 1, 2007, which claims benefit of U.S. Provisional Application No. 60/764,175, filed Feb. 1, 2006. U.S. application Ser. No. 11/670,318, filed Feb. 1, 2007, and U.S. Provisional Application No. 60/764,175, filed Feb. 1, 2006, are hereby incorporated herein by reference in their entirety.

STATEMENT REGARDING FEDERALLY SPONSORED RESEARCH

This invention was made with government support under Grants PO1 CA 82713, PO1 CA 104898, P30 CA 30199, RO1 CA115410 awarded by National Institutes of Health and Grants DAMD 17-02-1-0315, Grant T32 CA77109-05 awarded by the National Cancer Institute, and DAMD 17-02-0309 awarded by the Department of Defense. The government has certain rights in the invention.

REFERENCE TO SEQUENCE LISTING

The Sequence Listing submitted Feb. 10, 2011 as a text file named "SBMRI_26_8403 AMD_AFD_Sequence_Listing_Text_File," created on Feb. 2, 2011, and having a size of 15,594 bytes is hereby incorporated by reference pursuant to 37 C.F.R. §1.52(e)(5).

BACKGROUND

The endothelial lining of blood vessels is highly diversified. Many, perhaps all, normal tissues put a tissue-specific "signature" on their vasculature, and tumor vessels differ from normal vessels both in morphology and molecular composition (Ruoslahti, 2002). Tumors induce angiogenesis to accommodate the growth of the tumor (Hanahan and Weinberg, 2000) and many of the changes in tumor vessels are angiogenesis-related (Brooks et al., 1994; Christian et al., 2003; Ferrara and Alitalo, 1999; Pasqualini et al., 2000). Moreover, tumor blood vessels have tumor type-specific and, in some stages, stage-specific characteristics; in vivo screening of phage libraries yielded distinct sets of homing peptides selectively recognizing angiogenic signatures in two transgenic mouse models of organ specific tumorigenesis. Homing peptides can also distinguish the angiogenic blood vessels of pre-malignant lesions from those of fully malignant lesions in the same tumor model (Hoffman et al., 2003; Joyce et al., 2003), indicating that vascular changes mirror the stage of tumor development.

The lymphatic system constitutes a second vascular system, one that has only an efferent arm. Tumors frequently induce lymphangiogenesis, as well as co-opt existing lymphatics (Cao et al., 2004; Cassella and Skobe, 2002; Stacker et al., 2002). Tumors may contain intratumoral lymphatics, but, more commonly, an extensive network of lymphatic vessels is present around tumor tissue (Jackson et al., 2001; Laakkonen et al., 2002; Padera et al., 2002). The lymphatics within tumors, when present, are generally non-functional in fluid transport (Padera et al., 2002), possibly reflecting compression by interstitial pressure and blockade by intra-luminal tumor cells. The lymphatic vessels in and around tumors are an important conduit of metastasis. Indeed, growth factor-stimulated enhancement of lymphatic vessel expression in tumors increases metastasis (Mandriota et al., 2001; Skobe et al., 2001). Conversely, inhibiting lymphangigenesis suppresses lymphatic metastasis, but generally does not affect tumor growth (Saharinen et al., 2004).

As disclosed herein, tumor lymphatics, like tumor blood vessels, express specific markers, and that these lymphatic markers are tumor type-specific and distinct from blood vessel markers in the same tumors. Thus, needed in the art are compositions and methods for that selectively bind tumor lymphatics or lymphatics in pre-malignant lesions for use in early detection and tumor targeting.

BRIEF SUMMARY

In accordance with the purpose of this invention, as embodied and broadly described herein, this invention relates to peptides, compositions, conjugates, nucleic acids and methods for and involving selectively targeting tumor lymphatics and/or tumors and tumor cells.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

Figure 1:
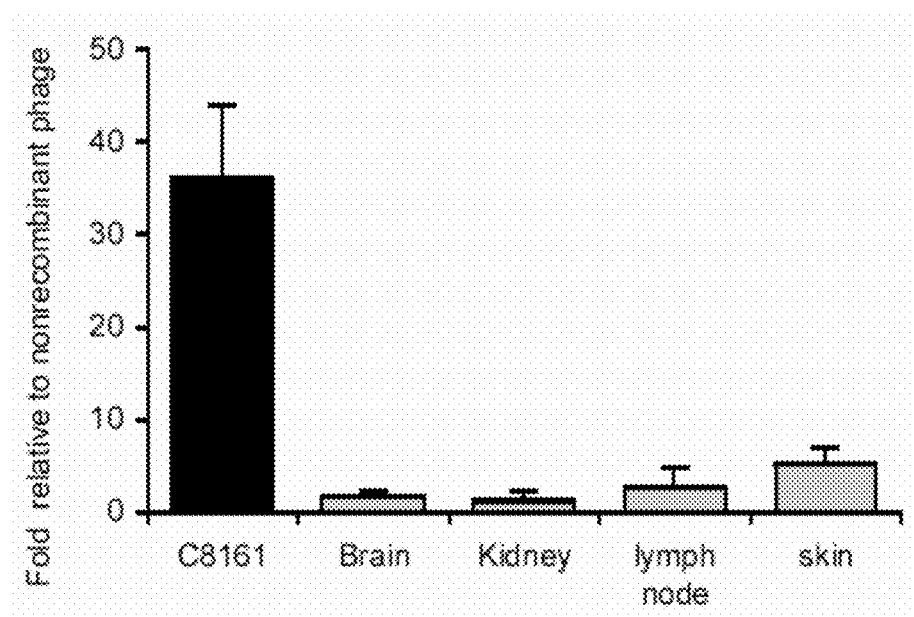
FIG. 1 shows a homing peptide recognizes C8161 melanoma lymphatics. Homing of LSD-phage to C8161 xenografts. The LSD phage clone ($2 \times 10^9$ pfu) was injected intravenously into mice bearing C8161 xenograft tumors and allowed to circulate for 7 min. Phage titers recovered from tumors and control tissues are shown. Phage accumulation in C8161 tumor tissue was significantly higher than in normal tissues. P<0.03 relative to the normal tissue with the highest phage uptake, the skin; (n=3).
Figure 4:
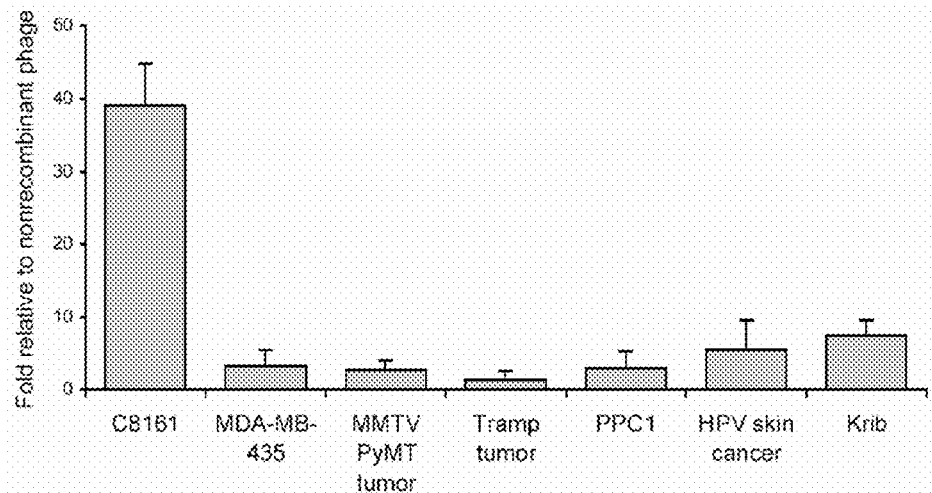

FIG. 4 shows tumor-type specificity of the LSD peptide. In vivo homing of the phage to six types of tumors was tested as in FIG. 1 (n=3 to 6). Robust phage homing was only observed in C8161 tumors. KRIB xenograft tumors were slightly positive for phage and peptide homing, but phage homing to C8161 tumors was significantly higher than to this or any of the other tumors (P<0.005).

Figure 5A:
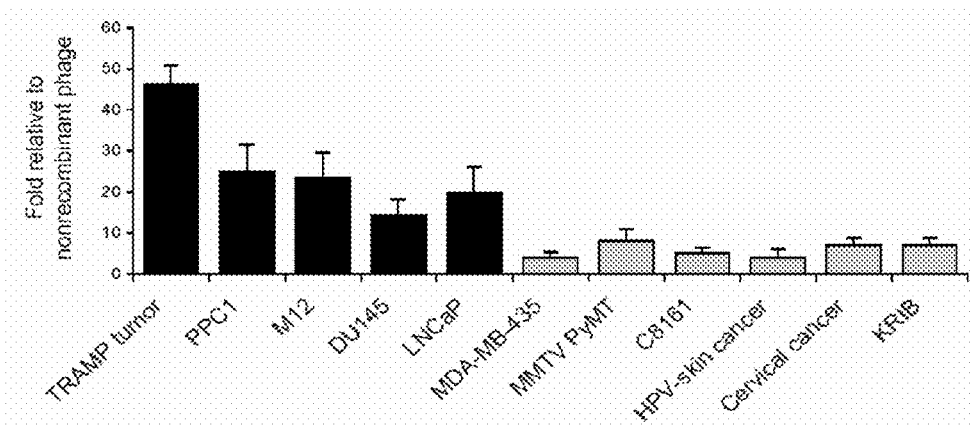
Figure 5B:
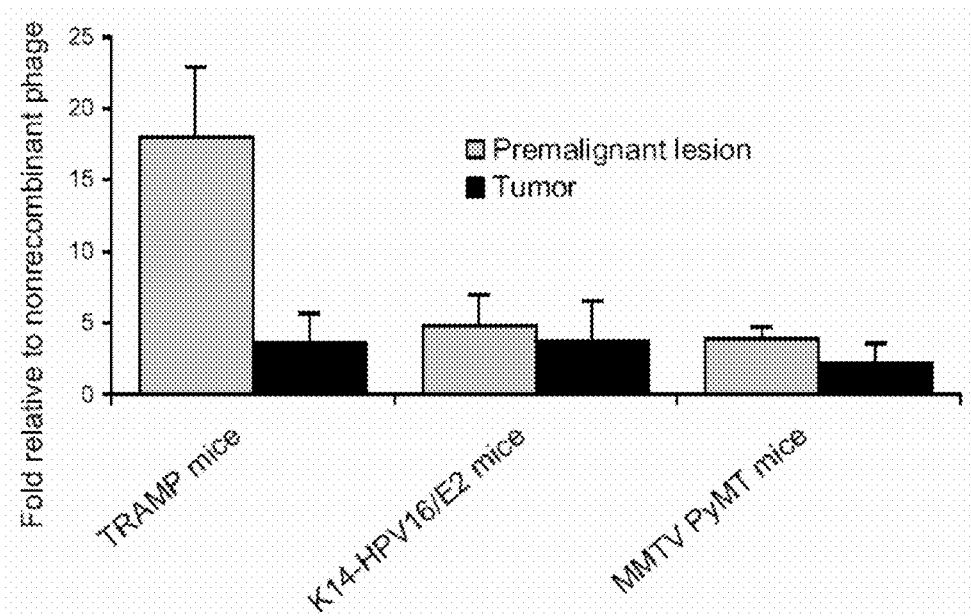

FIGS. 5A and 5B show homing specificity of the REA and AGR peptides in different types of tumors and pre-malignant lesions. In vivo homing of the REA-phage (A) to eleven types of tumors was tested (n=3 to 6). Significant phage homing was observed in prostate tumors of TRAMP mice, and in PPC1, M12, DU145 and LNCaP human prostate cancer xenograft tumors. Four out of 5 prostate cancers (DU145 was the exception) accumulated significantly more REA phage than the other types of tumors (P<0.03). Cervical tumors in K14-HPV16/E2 mice were slightly positive. FIG. 5B shows in vivo homing of intravenously injected AGR phage in TRAMP mice, K14-HPV16/E2 mice bearing CIN-3 lesions or tumors (n=3), and in MMTV-PyMT mice with dysplastic lesions or breast tumors. The AGR phage homed significantly more to TRAMP pre-malignant lesions than to comparable lesions in the other tumor models (P<0.03), and the TRAMP lesions are strongly positive for AGR peptide homing. A MMTVPyMT dysplastic breast lesion is weakly positive for AGR peptide binding.

Figures 6, 7A:
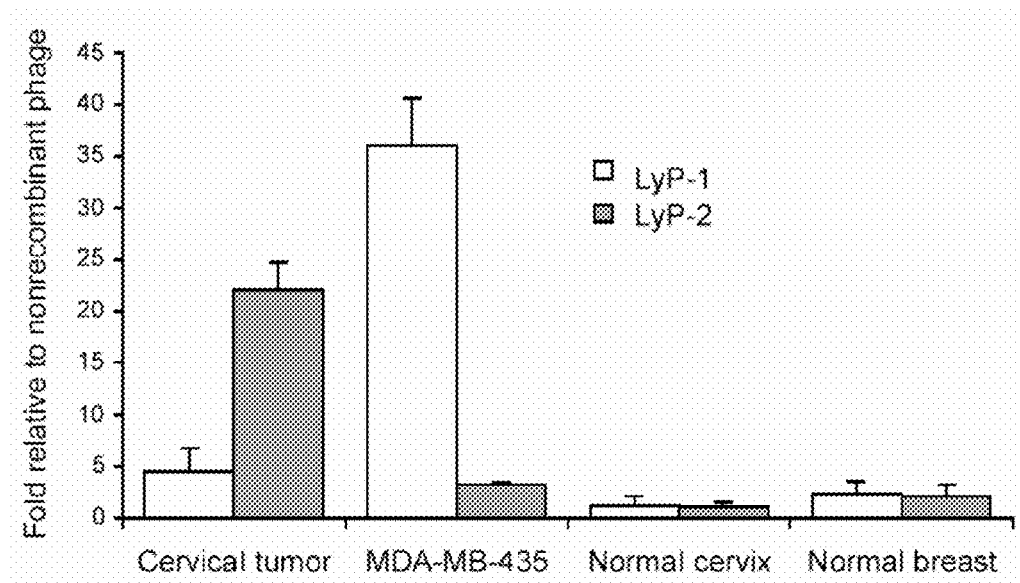

FIG. 6 shows differential tumor-homing specificity of LyP-1 and LyP-2 peptides. LyP-1 and LyP-2 phage were intravenously injected into mice bearing MDA-MB-435 breast cancer xenografts or K14-HPV16/E2 tumors (n=3). Tissues were collected and processed for histological analysis 2 hrs later. LyP-1 homes to the MDA-MB-435 tumors, whereas LyP-2 homes to the cervical cancers and pre-malignant lesions. Phage homing to the pre-malignant lesions was significantly higher than to the corresponding tumors in both models (P<0.01).

Figure 7B:
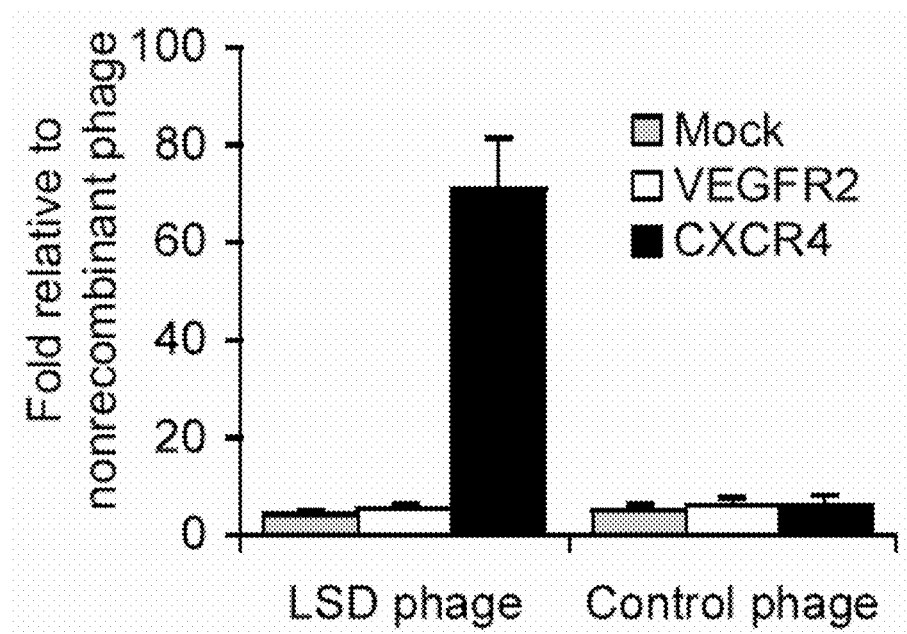
Figure 7C:
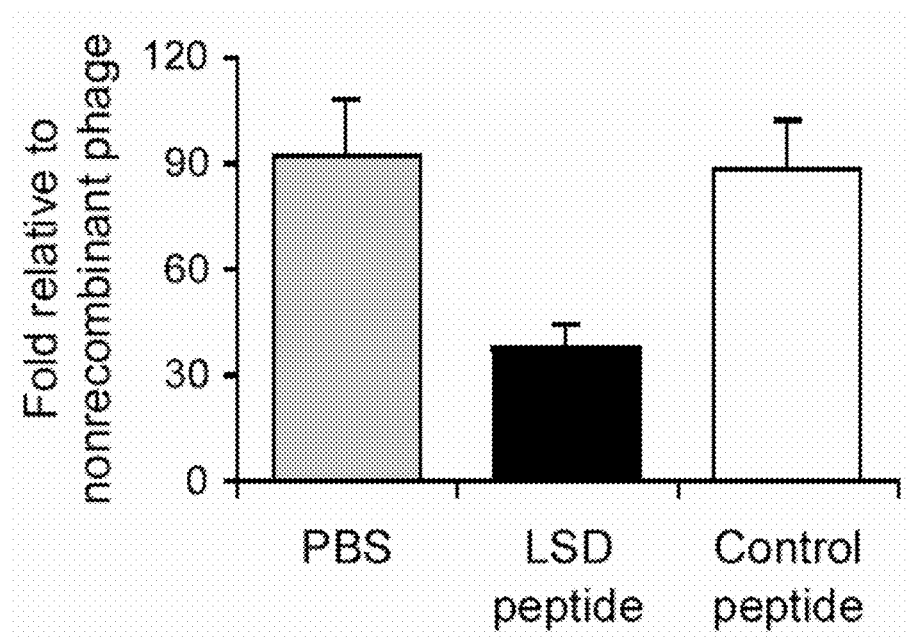

FIGS. 7A, 7B and 7C show transfection with the chemokine receptor CXCR4 increases the binding capability for the LSD peptide. FIG. 7A shows homology region with LSD peptide was found in residues 17-22 of pro-CXCL12 by searching NCBI BLAST against SWISSPROT database. FIG. 7B shows the LSD phage binds to 293T cells transfected with CXCR4, but not to cells transfected with VEGFR2 or with the empty vector (P<0.01). FIG. 7C shows the LSD peptide (150 µg/ml) inhibits LSD-phage binding to the CXCR4-transfected 293T cells (P<0.03). The LSD peptide with LSD-phage was co-incubated with CXCR4-transfected cells. Shown are the mean and standard deviation from three separate experiments.

Figure 8A:
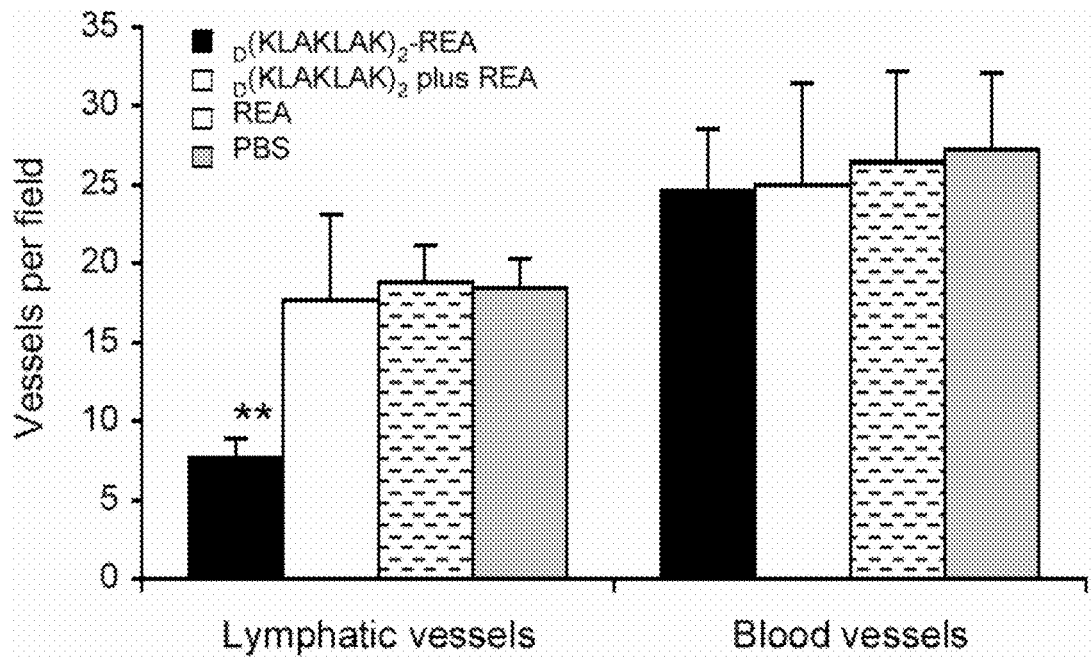
Figure 8B:
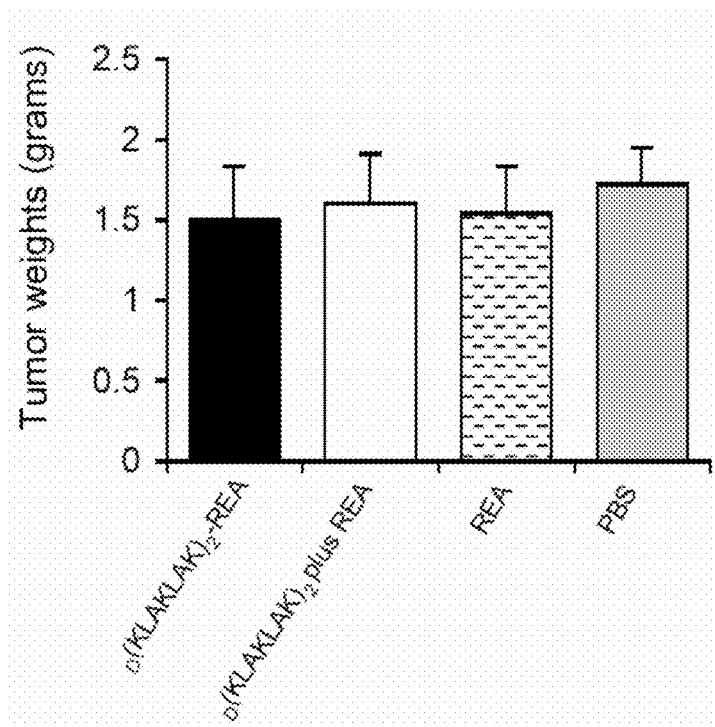

FIGS. 8A and 8B show targeting the tumor-associated lymphatics with homing peptides linked to a pro-apoptotic peptide. The PPC1 orthotopic xenografted mice (10 mice/group) were systemically treated with 100 µg/dose/mouse/biweekly of $_D$(KLAKLAK)$_2$-CREAGRKAC (SEQ ID NO:6), equimolar amounts of the uncoupled peptides, or with the vehicle (PBS). At termination, tumor weights were recorded, and frozen tissue sections were prepared for immunohistochemical analysis. The $_D$(KLAKLAK)$_2$-CREAGRKAC (SEQ ID NO:41) chimeric peptide greatly reduced the number of tumor lymphatics (P<0.01) as determined from podoplanin staining (A), whereas the blood vessel count (A; MECA-32 staining) and tumor volume (B) were unaffected.

Figure 9A:
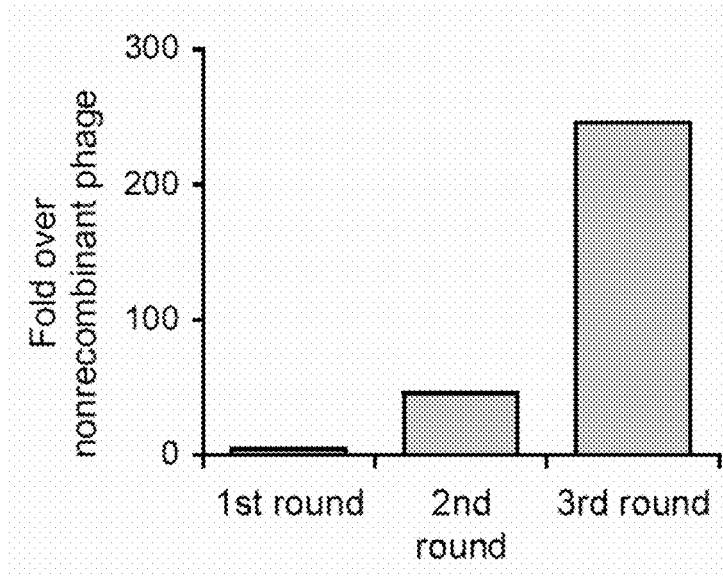
Figure 9B:
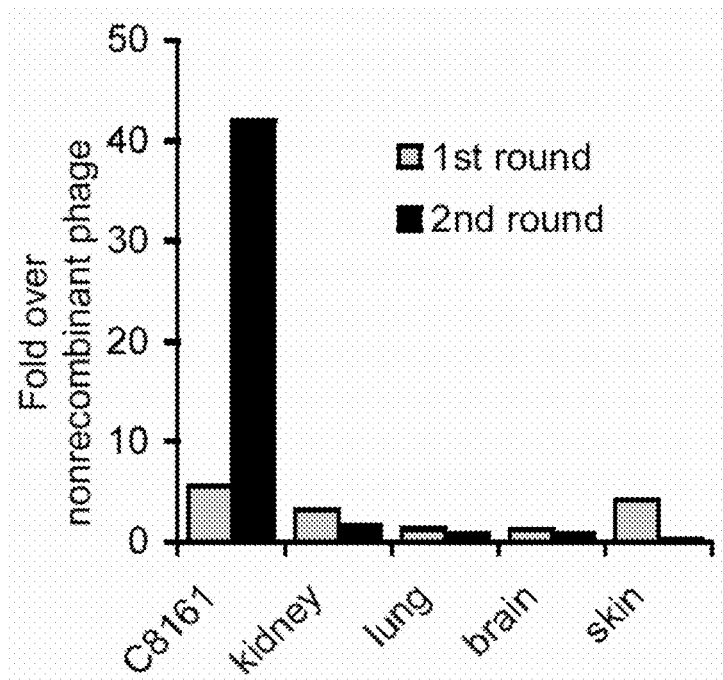

FIGS. 9A and 9B show phage library screening for peptides homing to lymphatic vessels in C8161 xenograft tumors. FIG. 9A shows ex vivo selection. The CX7C phage library ($5 \times 10^{10}$ pfu) was incubated with $5 \times 10^7$ cells derived from C8161 xenograft tumors at 4° C. overnight. Lymphatic endothelial cells were isolated with anti-mouse podoplanin captured onto magnetic beads. The phage that bound to lymphatic endothelial cells were rescued and amplified for subsequent screening. Three rounds of ex vivo selection yielded 250-fold enrichment of phage as compared to the background obtained with non-recombinant phage. FIG. 9B shows in vivo selection. The enriched phage pool from the third ex vivo selection round was injected into the tail vein of a C8161 tumor mouse. Phage were recovered from tumor tissue, amplified, and the selection was repeated. A 40-fold enrichment relative to non-recombinant phage was obtained in two in vivo rounds.

Figure 10A:
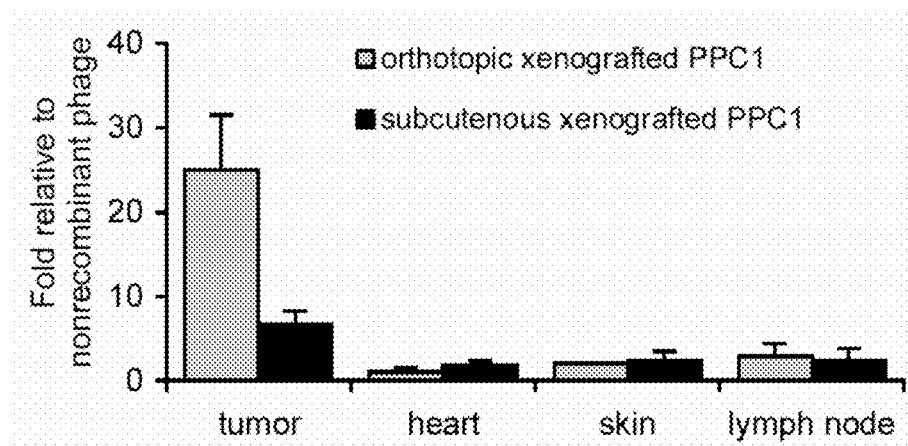
Figure 10B:
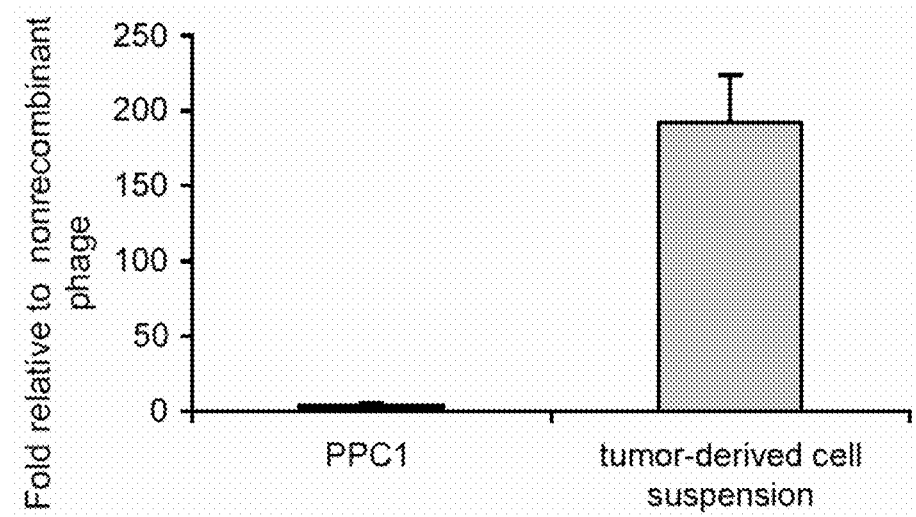

FIG. 10A shows comparison of the homing of REA phage to orthotopic vs. subcutaneously xenografted PPC1 tumors in nude mice. The REA phage ($5 \times 10^9$ pfu) were injected into tumor mice by tail vein. After circulation for 7 min, the bound phage were recovered from the tumors and various control organs and titrated (P<0.03 for orthotopic versus subcutaneous tumors; n=3). FIG. 10B shows REA-phage binds to cell suspensions derived from PPC1 tumors, but not to cultured PPC1 cells.

DETAILED DESCRIPTION

The disclosed method and compositions may be understood more readily by reference to the following detailed description of particular embodiments and the Example included therein and to the Figures and their previous and following description.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide is disclosed and discussed and a number of modifications that can be made to a number of molecules including the peptide are discussed, each and every combination and permutation of peptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Disclosed herein are peptides that selectively target tumor lymphatics. In some aspects, the disclosed peptides can selectively target lymphangiogenic vessels. In some aspects, the disclosed peptides can selectively bind markers present on tumor lymphatics. In some aspects, the disclosed peptides can selectively bind markers present on tumors and tumor cells. In some aspects, the disclosed peptides can selectively bind markers present on both tumors and tumor lymphatics. Thus, the disclosed peptides can be used, for example, to deliver moieties, such as therapeutic and/or detection moieties to tumor lymphatics, tumors, tumor cells and/or lymphangiogenic vessels. Also disclosed are methods of, for example, selectively targeting tumor lymphatics in a subject, selectively targeting a tumor cell in a subject, and selectively targeting tumor lymphatics and tumor cells.

The metastatic spread of tumor cells is the underlying cause of most cancer-related deaths. Clinical and pathological evidence confirms that the metastatic spread of tumors via lymphatic vessels to local/regional lymph nodes is an early event in metastatic disease for many solid human tumors. Tumors that secrete VEGF-C or VEGF-D induce lymphangiogenesis by activating VEGFR-3 on lymphatic vessels, a process known as tumor lymphangiogenesis. Lymphangiogenesis is the formation of lymphatic vessels from pre-existing lymphatic vessels, in a method believed to be similar to blood vessel development or angiogenesis. Lymphangiogenesis also plays an important physiological role in homeostasis, metabolism and immunity. Lymphatic vessel formation has also been implicated in a number of pathological conditions including neoplasm metastasis, oedema, rheumatoid arthritis, psoriasis and impaired wound healing.

As used herein, a "targeting peptide" is peptide or polypeptide that binds to a target, such as a cell. For example, a targeting peptide can display selective targeting activity. The terms "selective targeting" or "selective homing" as used herein each refer to a preferential localization of a compound or composition, such as the disclosed compositions, that results in an amount of the compound or composition in a target tissue that is, for example, about 2-fold greater than an amount of the peptide in a control tissue, about 5-fold or greater, or about 10-fold or greater. For example, the terms "selective targeting" and "selective homing" can refer to binding or accumulation of a compound or composition, such as the disclosed compositions in a target tissue concomitant with an absence of targeting to a control tissue or the absence of targeting to all control tissues.

A. Compositions

Disclosed herein are compositions and methods relating to novel peptides and conjugates that selectively target tumor lymphatics.

1. Peptides

Disclosed herein are peptides that target, bind to and/or home to tumor lymphatics, such as lymphatic vessels in and around tumors (which can also be referred to as tumor-associated lymphatic vessels), and/or lymphangiogenic vessels. The disclosed peptides preferably selectively bind to tumor lymphatics. The disclosed peptides can have a variety of structures. For example, in some forms, the amino acid sequence of the disclosed peptide can be CLSDGK (SEQ ID NO:2), CLSDGK (SEQ ID NO:2) with one, two or three conservative amino acid substitutions, CLSDGK (SEQ ID NO:2) with one non-conservative amino acid substitution, CLSDGK (SEQ ID NO:2) with one non-conservative amino acid substitution and one, two or three conservative amino acid substitutions, or a fragment of any of these forms having at least four consecutive amino acids. Also provided is an isolated peptide, wherein the peptide comprises an amino acid sequence, wherein the amino acid sequence has at least 70% sequence identity with CLSDGK (SEQ ID NO:2).

As a further example, the amino acid sequence of the disclosed peptide can be CLSDGKRKC (SEQ ID NO:4), CLSDGKRKC (SEQ ID NO:4) with one, two, three or four conservative amino acid substitutions, CLSDGKRKC (SEQ ID NO:4) with one, two or three non-conservative amino acid substitution, CLSDGKRKC (SEQ ID NO:4) with one, two or three non-conservative amino acid substitution and one, two, three or four conservative amino acid substitutions, or a fragment of any of these forms having at least four consecutive amino acids. Also provided is an isolated peptide, wherein the peptide comprises an amino acid sequence, wherein the amino acid sequence has at least 65% sequence identity with CLSDGKRKC (SEQ ID NO:4).

As a further example, the amino acid sequence of the disclosed peptide can be CLSDGKPVS (SEQ ID NO:3), CLSDGKPVS (SEQ ID NO:3) with one, two, three or four conservative amino acid substitutions, CLSDGKPVS (SEQ ID NO:3) with one, two or three non-conservative amino acid substitution, CLSDGKPVS (SEQ ID NO:3) with one, two or three non-conservative amino acid substitution and one, two, three or four conservative amino acid substitutions, or a fragment of any of these forms having at least four consecutive amino acids. Also provided is an isolated peptide, wherein the peptide comprises an amino acid sequence, wherein the amino acid sequence has at least 65% sequence identity with CLSDGKPVS (SEQ ID NO:3).

As a further example, the amino acid sequence of the disclosed peptide can be CASLSCR (SEQ ID NO:10), CASLSCR (SEQ ID NO:10) with one, two or three conservative amino acid substitutions, CASLSCR (SEQ ID NO:10) with one or two non-conservative amino acid substitution, CASLSCR (SEQ ID NO:10) with one or two non-conservative amino acid substitution and one, two or three conservative amino acid substitutions, or a fragment of any of these forms having at least four consecutive amino acids. Also provided is an isolated peptide, wherein the peptide comprises an amino acid sequence, wherein the amino acid sequence has at least 65% sequence identity with CASLSCR (SEQ ID NO:10).

As a further example, the amino acid sequence of the disclosed peptide can be CLDGGRPKC (SEQ ID NO:5), CLDGGRPKC (SEQ ID NO:5) with one, two, three or four conservative amino acid substitutions, CLDGGRPKC (SEQ ID NO:5) with one, two or three non-conservative amino acid substitution, CLDGGRPKC (SEQ ID NO:5) with one, two or three non-conservative amino acid substitution and one, two, three or four conservative amino acid substitutions, or a fragment of any of these forms having at least four consecutive amino acids. Also provided is an isolated peptide, wherein the peptide comprises an amino acid sequence, wherein the amino acid sequence has at least 65% sequence identity with CLDGGRPKC (SEQ ID NO:5).

As a further example, the amino acid sequence of the disclosed peptide can be CREAGRKAC (SEQ ID NO:6), CREAGRKAC (SEQ ID NO:6) with one, two, three or four conservative amino acid substitutions, CREAGRKAC (SEQ ID NO:6) with one, two or three non-conservative amino acid substitution, CREAGRKAC (SEQ ID NO:6) with one, two or three non-conservative amino acid substitution and one, two, three or four conservative amino acid substitutions, or a fragment of any of these forms having at least four consecutive amino acids. Also provided is an isolated peptide, wherein the peptide comprises an amino acid sequence, wherein the amino acid sequence has at least 65% sequence identity with CREAGRKAC (SEQ ID NO:6), As a further example, the amino acid sequence of the disclosed peptide can be CSMSAKKKC (SEQ ID NO:7), CSMSAKKKC (SEQ ID NO:7) with one, two, three or four conservative amino acid substitutions, CSMSAKKKC (SEQ ID NO:7) with one, two or three non-conservative amino acid substitution, CSMSAKKKC (SEQ ID NO:7) with one, two or three non-conservative amino acid substitution and one, two, three or four conservative amino acid substitutions, or a fragment of any of these forms having at least four consecutive amino acids. Also provided is an isolated peptide, wherein the peptide comprises an amino acid sequence, wherein the amino acid sequence has at least 65% sequence identity with CSMSAKKKC (SEQ ID NO:7).

As a further example, the amino acid sequence of the disclosed peptide can be CKTRVSCGV (SEQ ID NO:8), CKTRVSCGV (SEQ ID NO:8) with one, two, three or four conservative amino acid substitutions, CKTRVSCGV (SEQ ID NO:8) with one, two or three non-conservative amino acid substitution, CKTRVSCGV (SEQ ID NO:8) with one, two or three non-conservative amino acid substitution and one, two, three or four conservative amino acid substitutions, or a fragment of any of these forms having at least four consecutive amino acids. Also provided is an isolated peptide, wherein the peptide comprises an amino acid sequence, wherein the amino acid sequence has at least 65% sequence identity with CKTRVSCGV (SEQ ID NO:8).

As a further example, the amino acid sequence of the disclosed peptide can be CAGRRSAYC (SEQ ID NO:9), CAGRRSAYC (SEQ ID NO:9) with one, two, three or four conservative amino acid substitutions, CAGRRSAYC (SEQ ID NO:9) with one, two or three non-conservative amino acid substitution, CAGRRSAYC (SEQ ID NO:9) with one, two or three non-conservative amino acid substitution and one, two, three or four conservative amino acid substitutions, or a fragment of any of these forms having at least four consecutive amino acids. Also provided is an isolated peptide, wherein the peptide comprises an amino acid sequence, wherein the amino acid sequence has at least 65% sequence identity with CAGRRSAYC (SEQ ID NO:9).

As a further example, the amino acid sequence of the disclosed peptide can be CSGGKVLDC (SEQ ID NO:11), CSGGKVLDC (SEQ ID NO:11) with one, two, three or four conservative amino acid substitutions, CSGGKVLDC (SEQ ID NO:11) with one, two or three non-conservative amino acid substitution, CSGGKVLDC (SEQ ID NO:11) with one, two or three non-conservative amino acid substitution and one, two, three or four conservative amino acid substitutions, or a fragment of any of these forms having at least four consecutive amino acids. Also provided is an isolated peptide, wherein the peptide comprises an amino acid sequence, wherein the amino acid sequence has at least 65% sequence identity with CSGGKVLDC (SEQ ID NO:11).

As a further example, the peptide can comprise an amino acid sequence, where the amino acid sequence is XRTX (SEQ ID NO:59), where X is R or K (SEQ ID NOs:12-15). For example, the amino acid sequence of the disclosed peptide can be CGNKRTRGC (SEQ ID NO:16), CGNKRTRGC (SEQ ID NO:16) with one, two, three or four conservative amino acid substitutions, CGNKRTRGC (SEQ ID NO:16) with one, two or three non-conservative amino acid substitution, CGNKRTRGC (SEQ ID NO:16) with one, two or three non-conservative amino acid substitution and one, two, three or four conservative amino acid substitutions, or a fragment of any of these forms having at least four consecutive amino acids. Also provided is an isolated peptide, where the peptide comprises an amino acid sequence, wherein the amino acid sequence has at least 65% sequence identity with CGNKRTRGC (SEQ ID NO:16). In some aspects, the amino acid sequence of the disclosed peptide does not consist of CGNKRTRGC (SEQ ID NO:16).

As a further example, the amino acid sequence of the disclosed peptide can be CNRRTKAGC (SEQ ID NO:17), CNRRTKAGC (SEQ ID NO:17) with one, two, three or four conservative amino acid substitutions, CNRRTKAGC (SEQ ID NO:17) with one, two or three non-conservative amino acid substitution, CNRRTKAGC (SEQ ID NO:17) with one, two or three non-conservative amino acid substitution and one, two, three or four conservative amino acid substitutions, or a fragment of any of these forms having at least four consecutive amino acids. Also provided is an isolated peptide, where the peptide comprises an amino acid sequence, wherein the amino acid sequence has at least 65% sequence identity with CNRRTKAGC (SEQ ID NO:17). In some aspects, the amino acid sequence of the disclosed peptide does not consist of CNRRTKAGC (SEQ ID NO:17).

As a further example, the amino acid sequence of the disclosed peptide can be CNKRTRGGC (SEQ ID NO:18), CNKRTRGGC (SEQ ID NO:18) with one, two, three or four conservative amino acid substitutions, CNKRTRGGC (SEQ ID NO:18) with one, two or three non-conservative amino acid substitution, CNKRTRGGC (SEQ ID NO:18) with one, two or three non-conservative amino acid substitution and one, two, three or four conservative amino acid substitutions, or a fragment of any of these forms having at least four consecutive amino acids. Also provided is an isolated peptide, where the peptide comprises an amino acid sequence, wherein the amino acid sequence has at least 65% sequence identity with CNKRTRGGC (SEQ ID NO:18). In some aspects, the amino acid sequence of the disclosed peptide does not consist of CNKRTRGGC (SEQ ID NO:18).

As a further example, the amino acid sequence of the disclosed peptide can consist of CLSDGK (SEQ ID NO:2), CASLSCR (SEQ ID NO:10), CLDGGRPKC (SEQ ID NO:5), CREAGRKAC (SEQ ID NO:6), CSMSAKKKC (SEQ ID NO:7), CKTRVSCGV (SEQ ID NO:8), CAGRRSAYC (SEQ ID NO:9), CSGGKVLDC (SEQ ID NO:11), CGNKRTRGC (SEQ ID NO:16), CNRRTKAGC (SEQ ID NO:17), CNKRTRGGC (SEQ ID NO:18), CLSDGKRKC (SEQ ID NO:4), or CLSDGKPVS (SEQ ID NO:3).

The disclosed peptide can have any suitable length. For example, the peptide can have a length of up to 25, 26, 27, 28, 29, 30, 31, 32, 33, 34, 35, 36, 37, 38, 39, 40, 41, 42, 43, 44, 45, 46, 47, 48, 49, or 50 amino acids. The disclosed polypeptides can be, for example, 4 to about 50 amino acids in length. The disclosed polypeptides can be, for example, less than about 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, or 4 amino acids in length.

For example, the disclosed peptide can have a length of from 4 to about 10 amino acids, from 4 to about 15 amino acids, from 4 to about 20 amino acids, from 4 to about 25 amino acids, from 4 to about 30 amino acids, from 4 to about 35 amino acids, from 4 to about 40 amino acids, from 4 to about 45 amino acids, from 4 to about 50 amino acids. For example, the disclosed peptide can have a length of from 5 to about 10 amino acids, from 5 to about 15 amino acids, from 5 to about 20 amino acids, from 5 to about 25 amino acids, from 5 to about 30 amino acids, from 5 to about 35 amino acids, from 5 to about 40 amino acids, from 5 to about 45 amino acids, from 5 to about 50 amino acids. For example, the disclosed peptide can have a length of from 6 to about 10 amino acids, from 6 to about 15 amino acids, from 6 to about 20 amino acids, from 6 to about 25 amino acids, from 6 to about 30 amino acids, from 6 to about 35 amino acids, from 6 to about 40 amino acids, from 6 to about 45 amino acids, from 6 to about 50 amino acids. For example, the disclosed peptide can have a length of from 7 to about 10 amino acids, from 7 to about 15 amino acids, from 7 to about 20 amino acids, from 7 to about 25 amino acids, from 7 to about 30 amino acids, from 7 to about 35 amino acids, from 7 to about 40 amino acids, from 7 to about 45 amino acids, from 7 to about 50 amino acids. For example, the disclosed peptide can have a length of from 8 to about 10 amino acids, from 8 to about 15 amino acids, from 8 to about 20 amino acids, from 8 to about 25 amino acids, from 8 to about 30 amino acids, from 8 to about 35 amino acids, from 8 to about 40 amino acids, from 8 to about 45 amino acids, from 8 to about 50 amino acids. For example, the disclosed peptide can have a length of from 9 to about 10 amino acids, from 9 to about 15 amino acids, from 9 to about 20 amino acids, from 9 to about 25 amino acids, from 9 to about 30 amino acids, from 9 to about 35 amino acids, from 9 to about 40 amino acids, from 9 to about 45 amino acids, from 9 to about 50 amino acids.

The disclosed peptides can be artificial sequences and can be synthesized in vitro and/or recombinantly. The disclosed polypeptides can be peptides that are not naturally occurring proteins and can be peptides that have at least two contiguous sequences that are not contiguous in a naturally occurring protein.

The disclosed peptides and compositions also can comprise any combination of two, three, or more of the disclosed peptides or amino acid sequences. Thus, disclosed are peptides comprising any one, two, three, or more of the herein disclosed peptides or amino acid sequences. The peptides can be combined in any suitable manner, including, for example, as a single amino acid chain (that is a fusion of the peptides), via linkers, via branched linkers, and attached individually or together to a structure. Also disclosed are bifunctional peptides, which contain one or more of the disclosed peptides fused to one or more second peptides having one or more separate functions. Such bifunctional peptides can have at least two functions conferred by different portions of the full-length molecule and can, for example, display pro-apoptotic activity in addition to the ability to target the tumor lymphatic.

Also disclosed are multivalent peptides that can include at least two of the disclosed peptides each independently containing one or more of the disclosed amino acid sequences. The multivalent peptide can have, for example, at least three, at least five or at least ten of such peptides each independently containing a disclosed amino acid sequence. In some aspects, the multivalent peptide can have two, three, four, five, six, seven, eight, nine, ten, fifteen or twenty identical or non-identical peptides and/or amino acid sequences. In some aspects, the multivalent peptide can contain identical peptides and/or amino acid sequences. In some aspects, the multivalent peptide can contain contiguous identical or non-identical peptides and/or amino acid sequences, which are or are not separated by any intervening amino acids.

2. Conjugate

Also provided herein is a conjugate comprising any one or more of the herein disclosed peptides and one or more moieties. In general, the moiety can be a substance that acts upon the target cell(s) or tissue to bing about a desired effect. In some aspects, the disclosed conjugate can target, bind to and/or home to tumor lymphatics, such as lymphatic vessels in and around tumors, and/or lymphangiogenic vessels. The disclosed peptides preferably selectively bind to tumor lymphatics. Thus, the effect can, for example, be the labeling, activating, repressing, or killing of the target cell(s) or tissue.

The moiety can be, for example, a therapeutic moiety or a detectable moiety, a cytotoxic agent, an anti-lymphangiogenic agent, a cancer chemotherapeutic agent, a pro-apoptotic polypeptide, a grafted polypeptide, a virus, a cell, or a liposome. Thus, the moiety can be a small molecule, pharmaceutical drug, toxin, fatty acid, detectable marker, conjugating tag, nanoparticle, or enzyme. For example, the moiety of the disclosed conjugate can be a pro-apoptotic peptide. Examples of pro-apoptotic peptides are the amino acid sequence $_D$(KLAKLAK)$_2$ (SEQ ID NO:19), tumor necrosis factor (Curnis et al., Cancer Res. 64, 565-71, 2004) and tachyplesin (Chen et al., Cancer res. 61, 2434-8, 2001). Many other pro-apoptotic peptides and compounds are known and can be used with and in the disclosed compositions, conjugates and methods.

Examples of small molecules and pharmaceutical drugs that can be conjugated to a peptide are known in the art. The moiety can be a cytotoxic small molecule or drug that kills the target cell. The small molecule or drug can be designed to act on any critical cellular function or pathway. For example, the small molecule or drug can inhibit the cell cycle, activate protein degradation, induce apoptosis, modulate kinase activity, or modify cytoskeletal proteins. Any known or newly discovered cytotoxic small molecule or drugs is contemplated for use with the peptides.

The moiety can be a toxin that kills the targeted cell. Non-limiting examples of toxins include abrin, modeccin, ricin and diphtheria toxin. Other known or newly discovered toxins are contemplated for use with the provided conjugates.

Fatty acids (i.e., lipids) that can be conjugated to the provided conjugates include those that allow the efficient incorporation of the peptide into liposomes. Generally, the fatty acid is a polar lipid. Thus, the fatty acid can be a phospholipid. The provided conjugates can comprise either natural or synthetic phospholipid. The phospholipids can be selected from phospholipids containing saturated or unsaturated mono or disubstituted fatty acids and combinations thereof. These phospholipids can be dioleoylphosphatidylcholine, dioleoylphosphatidylserine, dioleoylphosphatidylethanolamine, dioleoylphosphatidylglycerol, dioleoylphosphatidic acid, palmitoyloleoylphosphatidylcholine, palmitoyloleoylphosphatidylserine, palmitoyloleoylphosphatidylethanolamine, palmitoyloleoylphophatidylglycerol, palmitoyloleoylphosphatidic acid, palmitelaidoyloleoylphosphatidylcholine, palmitelaidoyloleoylphosphatidylserine, palmitelaidoyloleoylphosphatidylethanolamine, palmitelaidoyloleoylphosphatidylglycerol, palmitelaidoyloleoylphosphatidic acid, myristoleoyloleoylphosphatidylcholine, myristoleoyloleoylphosphatidylserine, myristoleoyloleoylphosphatidylethanoamine, myristoleoyloleoylphosphatidylglycerol, myristoleoyloleoylphosphatidic acid, dilinoleoylphosphatidylcholine, dilinoleoylphosphatidylserine, dilinoleoylphosphatidylethanolamine, dilinoleoylphosphatidylglycerol, dilinoleoylphosphatidic acid, palmiticlinoleoylphosphatidylcholine, palmiticlinoleoylphosphatidylserine, palmiticlinoleoylphosphatidylethanolamine, palmiticlinoleoylphosphatidylglycerol, palmiticlinoleoylphosphatidic acid. These phospholipids may also be the monoacylated derivatives of phosphatidylcholine (lysophophatidylidylcholine), phosphatidylserine (lysophosphatidylserine), phosphatidylethanolamine (lysophosphatidylethanolamine), phophatidylglycerol (lysophosphatidylglycerol) and phosphatidic acid (lysophosphatidic acid). The monoacyl chain in these lysophosphatidyl derivatives may be palimtoyl, oleoyl, palmitoleoyl, linoleoyl myristoyl or myristoleoyl. The phospholipids can also be synthetic. Synthetic phospholipids are readily available commercially from various sources, such as AVANTI Polar Lipids (Albaster, Ala.); Sigma Chemical Company (St. Louis, Mo.). These synthetic compounds may be varied and may have variations in their fatty acid side chains not found in naturally occurring phospholipids. The fatty acid can have unsaturated fatty acid side chains with C14, C16, C18 or C20 chains length in either or both the PS or PC. Synthetic phospholipids can have dioleoyl (18:1)-PS; palmitoyl (16:0)-oleoyl (18:1)-PS, dimyristoyl (14:0)-PS; dipalmitoleoyl (16:1)-PC, dipalmitoyl (16:0)-PC, dioleoyl (18:1)-PC, palmitoyl (16:0)-oleoyl (18:1)-PC, and myristoyl (14:0)-oleoyl (18:1)-PC as constituents. Thus, as an example, the provided conjugates can comprise palmitoyl 16:0.

The moiety of the disclosed conjugate can be a detection moiety. Detectable moieties/markers include any substance that can be used to label or stain a target tissue or cell(s). Non-limiting examples of detectable markers include radioactive isotopes, enzymes, fluorophores, and quantum dots (Qdot®). For example, the detection moiety can be an enzyme, biotin, metal, or epitope tag. Other known or newly discovered detectable markers are contemplated for use with the provided conjugates.

Fluorophores are compounds or molecules that luminesce. Typically fluorophores absorb electromagnetic energy at one wavelength and emit electromagnetic energy at a second wavelength. Representative fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Dil (DilC18(3)); I Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); FITC; Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA);

LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; PhotoResist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (Pl); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodamineIsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

The moiety can be a nanoparticle, such as a heat generating nanoshell. As used herein, "nanoshell" is a nanoparticle having a discrete dielectric or semi-conducting core section surrounded by one or more conducting shell layers. U.S. Pat. No. 6,530,944 is hereby incorporated by reference herein in its entirety for its teaching of the methods of making and using metal nanoshells. Nanoshells can be formed with a core of a dielectric or inert material such as silicon, coated with a material such as a highly conductive metal which can be excited using radiation such as near infrared light (approximately 800 to 1300 nm). Upon excitation, the nanoshells emit heat. The resulting hyperthermia can kill the surrounding cell(s) or tissue. The combined diameter of the shell and core of the nanoshells ranges from the tens to the hundreds of nanometers. Near infrared light is advantageous for its ability to penetrate tissue. Other types of radiation can also be used, depending on the selection of the nanoparticle coating and targeted cells. Examples include x-rays, magnetic fields, electric fields, and ultrasound. The particles can also be used to enhance imaging, especially using infrared diffuse photon imaging methods. Targeting molecules can be antibodies or fragments thereof, ligands for specific receptors, or other proteins specifically binding to the surface of the cells to be targeted.

The moiety can be covalently linked to the disclosed peptide. The moiety can be linked to the amino terminal end of the disclosed peptide. The moiety can be linked to the carboxy terminal end of the disclosed peptide. The moiety can be linked to an amino acid within the disclosed peptide. The herein provided conjugates can further comprise a linker connecting the moiety and disclosed peptide. The disclosed peptide can also be conjugated to a coating molecule such as bovine serum albumin (BSA) (see Tkachenko et al., (2003) J Am Chem Soc, 125, 4700-4701) that can be used to coat the Nanoshells with the peptide.

Protein crosslinkers that can be used to crosslink the moiety to the disclosed peptide are known in the art and are defined based on utility and structure and include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy) ethyl]sulfone), BSOCOES (Bis[2-(succinimdooxycarbonyloxy)ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis (sulfosuccinimidylsuccinate)), DPDPB (1,2-Di[3'-(2'-pyridyldithio) propionamido]butane), BSSS (Bis (sulfosuccinimdyl) suberate), SMPB (Succinimdyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl)aminobenzoate), SULFO SIAB (N-Sulfosuccinimidyl(4-iodoacetyl)aminobenzoate), SMCC (Succinimidyl-4-(N-maleimidomethyl)cyclohexane-1-carboxylate), SULFO SMCC (Sulfosuccinimidyl-4-(N-maleimidomethyl)cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl)cyclohexane-1-carboxylic acid hydrazide hydrochloride), MBH (m-Maleimidobenzoic acid hydrazidehydrochloride), SULFO EMCS(N-(epsilon-Maleimidocaproyloxy) sulfosuccinimide), EMCS(N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), DMA (Dimethyladipimidate hydrochloride).

The moiety of the disclosed conjugate can be a cellular internalization transporter or sequence. The cellular internalization sequence can be any internalization sequence known or newly discovered in the art, or conservative variants thereof. Non-limiting examples of cellular internalization transporters and sequences include Antennapedia sequences, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, BGSC (Bis-Guanidinium-Spermidine-Cholesterol, and BGTC (Bis-Guanidinium-Tren-Cholesterol) (see Table 1).

Thus, the provided polypeptide can further comprise the amino acid sequence SEQ ID NO:44, SEQ ID NO:45 (Bucci, M. et al. 2000. Nat. Med. 6, 1362-1367), SEQ ID NO:46 (Derossi, D., et al. 1994. Biol. Chem. 269, 10444-10450), SEQ ID NO:47 (Fischer, P. M. et al. 2000. J. Pept. Res. 55, 163-172), SEQ ID NO:48 (Frankel, A. D. & Pabo, C. O. 1988. Cell 55, 1189-1193; Green, M. & Loewenstein, P. M. 1988. Cell 55, 1179-1188), SEQ ID NO:49 (Park, C. B., et al. 2000. Proc. Natl. Acad. Sci. USA 97, 8245-8250), SEQ ID NO:50 (Pooga, M., et al. 1998. FASEB J. 12, 67-77), SEQ ID NO:51 (Oehlke, J. et al. 1998. Biochim. Biophys. Acta. 1414, 127-139), SEQ ID NO:52 (Lin, Y. Z., et al. 1995. J. Biol. Chem. 270, 14255-14258), SEQ ID NO:53 (Sawada, M., et al. 2003. Nature Cell Biol. 5, 352-357), SEQ ID NO:54 (Lundberg, P. et al. 2002. Biochem. Biophys. Res. Commun. 299, 85-90), SEQ ID NO:55 (Elmquist, A., et al. 2001. Exp. Cell Res. 269, 237-244), SEQ ID NO:56 (Morris, M. C., et al. 2001. Nature Biotechnol. 19, 1173-1176), SEQ ID NO:57 (Rousselle, C. et al. 2000. Mol. Pharmacol. 57, 679-686), SEQ ID NO:58 (Gao, C. et al. 2002. Bioorg. Med. Chem. 10, 4057-4065), or SEQ ID NO:59 (Hong, F. D. & Clayman, G. L. 2000. Cancer Res. 60, 6551-6556). The provided polypeptide can further comprise BGSC (Bis-Guanidinium-Spermidine-Choles-

TABLE 1

Cell Internalization Transporters

| Name | Sequence | SEQ ID NO |
|---|---|---|
| Antp | RQPKIWFPNRRKPWKK | (SEQ ID NO: 44) |
| HIV-Tat | GRKKRRQRPPQ | (SEQ ID NO: 45) |
| Penetratin | RQIKIWFQNRRMKWKK | (SEQ ID NO: 46) |
| Antp-3A | RQIAIWFQNRRMKWAA | (SEQ ID NO: 47) |
| Tat | RKKRRQRRR | (SEQ ID NO: 48) |
| Buforin II | TRSSRAGLQFPVGRVHRLLRK | (SEQ ID NO: 49) |
| Transportan | GWTLNSAGYLLGKINKALAALAKKIL | (SEQ ID NO: 50) |
| model amphipathic peptide (MAP) | KLALKLALKALKAALKLA | (SEQ ID NO: 51) |
| K-FGF | AAVALLPAVLLALLAP | (SEQ ID NO: 52) |
| Ku70 | VPMLK-PMLKE | (SEQ ID NO: 53) |
| Prion | MANLGYWLLALFVTMWTDVGLCKKRPKP | (SEQ ID NO: 54) |
| pVEC | LLIILRRRIRKQAHAHSK | (SEQ ID NO: 55) |
| Pep-1 | KETWWETWWTEWSQPKKKRKV | (SEQ ID NO: 56) |
| SynB1 | RGGRLSYSRRRFSTSTGR | (SEQ ID NO: 57) |
| Pep-7 | SDLWEMMMVSLACQY | (SEQ ID NO: 58) |
| HN-1 | TSPLNIHNGQKL | (SEQ ID NO: 59) |

BGSC (Bis-Guanidinium-Spermidine-Cholesterol)

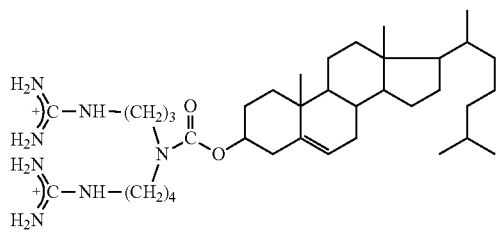

BGSC

BGTC (Bis-Guanidinium-Tren-Cholesterol)

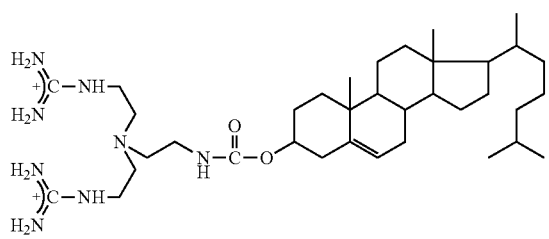

BGTC terol) or BGTC (Bis-Guanidinium-Tren-Cholesterol) (Vigneron, J. P. et al. 1998. Proc. Natl. Acad. Sci. USA. 93, 9682-9686). The preceding references are hereby incorporated herein by reference in their entirety for the teachings of cellular internalization vectors and sequences. Any other internalization sequences now known or later identified can be combined with a polypeptide disclosed herein.

3. Polypeptides and Peptides i. Protein Variants

Protein variants and derivatives are well understood by those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof can be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 2 and are referred to as conservative substitutions.

TABLE 2

Amino Acid Substitutions
Original Residue Exemplary Conservative
Substitutions, others are known in the art.

| Ala | Ser |
|---|---|
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |

TABLE 2-continued

Amino Acid Substitutions
Original Residue Exemplary Conservative
Substitutions, others are known in the art.

| Leu | Ile; Val |
|---|---|
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

Specifically disclosed are variants of these and other polypeptides herein disclosed which have at least, 65%, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed peptides. For example, there are numerous D amino acids or amino acids which have a different functional substituent than the amino acids shown in Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10): 400-403 (1989); Benner, TIB Tech, 12:158-163 (1994); Ibba and Hennecke, Bio/technology, 12:678-682 (1994) all of which are herein) incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2$—$CH_2$ (cis and trans), —$COCH_2$—$CH(OH)CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. 1307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—$CH(OH)CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

4. Nucleic Acid

Also provided herein is an isolated nucleic acid encoding any of the herein disclosed peptides. Also provided herein is an isolated nucleic acid encoding any of the herein disclosed peptides further comprising a nucleic acid encoding a internalization sequence. For example, the cellular internalization can comprise an amino acid sequence of a protein selected from a group consisting of Antennapedia, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol and BGTC (Bis-Guanidinium-Tren-Cholesterol.

i. Nucleotides and Related Molecules

The disclosed nucleic acids can be made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties. There are many varieties of these types of molecules available in the art and available herein.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid. There are many varieties of these types of molecules available in the art and available herein.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556). There are many varieties of these types of molecules available in the art and available herein.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

5. Cell Delivery Systems

Also provided is a vector comprising a nucleic acid encoding a polypeptide disclosed herein, wherein the nucleic acid is operably linked to an expression control sequence. There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

i. Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acid into the cell without degradation and include a promoter yielding expression of the gene in the cells into which it is delivered. Viral vectors include, for example, Adenovirus, Adeno-associated virus, Herpes virus, Vaccinia virus, Polio virus, AIDS virus, neuronal trophic virus, Sindbis and other RNA viruses; including these viruses with the HIV backbone. Also disclosed are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. Disclosed is a viral vector that has been engineered to suppress the immune response of the host organism, elicited by the viral antigens. Example vectors of this type can carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

a. Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

b. Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virions are generated in a cell line such as the human 293 cell line. In another preferred embodiment both the E1 and E3 genes are removed from the adenovirus genome.

c. Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

d. Large Payload Viral Vectors

Molecular genetic experiments with large human herpesviruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

ii. Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise lipids such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Feigner et al. Proc. Natl. Acad. Sci. USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials can be in solution, suspension (for example, incorporated into microparticles, liposomes, or cells). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

iii. In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

iv. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and can contain upstream elements and response elements.

a. Viral Promoters and Enhancers

Preferred promoters controlling transcription from vectors in mammalian host cells can be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell. Bio. 4: 1293 (1984)). They are usually between 10 and 300 by in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, $\alpha$-fetoprotein and insulin), typically, one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer can be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) can also contain sequences necessary for the termination of transcription which can affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b. Markers

The viral vectors can include nucleic acid sequence encoding a marker product. This marker product is used to determine if the gene has been delivered to the cell and once delivered is being expressed. Preferred marker genes are the E. Coli lacZ gene, which encodes β-galactosidase, and green fluorescent protein.

In some embodiments the marker can be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1:327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

6. Sequence Similarities

It is understood that as discussed herein the use of the terms homology and identity mean the same thing as similarity. Thus, for example, if the use of the word homology is used between two non-natural sequences it is understood that this is not necessarily indicating an evolutionary relationship between these two sequences, but rather is looking at the similarity or relatedness between their nucleic acid sequences. Many of the methods for determining homology between two evolutionarily related molecules are routinely applied to any two or more nucleic acids or proteins for the purpose of measuring sequence similarity regardless of whether they are evolutionarily related or not.

In general, it is understood that one way to define any known variants and derivatives or those that might arise, of the disclosed genes and proteins herein, is through defining the variants and derivatives in terms of homology to specific known sequences. This identity of particular sequences disclosed herein is also discussed elsewhere herein. In general, variants of genes and proteins herein disclosed typically have at least about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology to the stated sequence or the native sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison can be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

7. Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization can involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 8), 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

8. Antibodies

Also disclosed herein are antibodies that specifically bind any of the peptides or polypeptides disclosed herein. The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to interact with a polypeptides disclosed herein.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity (See, U.S. Pat. No. 4,816,567 and Morrison et al., Proc. Natl. Acad. Sci. USA, 81:6851-6855 (1984)).

The disclosed monoclonal antibodies can be made using any procedure which produces mono clonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes can be immunized in vitro, e.g., using the HIV Env-CD4-co-receptor complexes described herein.

The monoclonal antibodies can also be made by recombinant DNA methods, such as those described in U.S. Pat. No. 4,816,567 (Cabilly et al.). DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

The disclosed human antibodies can be prepared using any technique. Examples of techniques for human monoclonal antibody production include those described by Cole et al. (Monoclonal Antibodies and Cancer Therapy, Alan R. Liss, p. 77, 1985) and by Boerner et al. (J. Immunol., 147(1):86-95, 1991). Human antibodies (and fragments thereof) can also be produced using phage display libraries (Hoogenboom et al., J. Mol. Biol., 227:381, 1991; Marks et al., J. Mol. Biol., 222: 581, 1991).

The disclosed human antibodies can also be obtained from transgenic animals. For example, transgenic, mutant mice that are capable of producing a full repertoire of human antibodies, in response to immunization, have been described (see, e.g., Jakobovits et al., Proc. Natl. Acad. Sci. USA, 90:2551-255 (1993); Jakobovits et al., Nature, 362:255-258 (1993); Bruggermann et al., Year in Immunol., 7:33 (1993)). Specifically, the homozygous deletion of the antibody heavy chain joining region (J(H)) gene in these chimeric and germ-line mutant mice results in complete inhibition of endogenous antibody production, and the successful transfer of the human germ-line antibody gene array into such germ-line mutant mice results in the production of human antibodies upon antigen challenge. Antibodies having the desired activity are selected using Env-CD4-co-receptor complexes as described herein.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies can also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., Science, 239:1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

9. Pharmaceutical Carriers

The disclosed compositions can be used therapeutically in combination with a pharmaceutically acceptable carrier. By "pharmaceutically acceptable" is meant a material that is not biologically or otherwise undesirable, i.e., the material can be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions can include carriers, thickeners, diluents, buffers, preservatives, surface active agents and the like in addition to the molecule of choice. Pharmaceutical compositions can also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, antioxidants, chelating agents, and inert gases and the like.

Formulations for topical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The materials can be in solution, suspension (for example, incorporated into microparticles, liposomes, or cells). These can be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

B. Methods

1. Targeting

Provided herein is a method of targeting one or more moieties to tumor lymphatics in a subject. The method can involve administering to the subject a conjugate comprising any one or more of the herein disclosed peptides and the one or more moieties. The one or more moieties can be detection moieties, such as those disclosed herein. Thus, the method can further comprise detecting the tumor in the subject by detecting the presence of the conjugate in the lymphatics of the subject.

The one or more moieties can be therapeutic moieties, such as those disclosed herein. Thus, wherein the subject has cancer, targeting of the moiety to the tumor lymphatics of the subject can inhibit lymphangiogenesis in the tumor in the subject.

2. Detecting

Also provided is a method of detecting cancer. The method can involve contacting a biological sample with a conjugate comprising any one or more of the herein disclosed peptides and one or more moieties, and detecting the presence of the conjugate in lymphatics of the sample. In some aspects of the disclosed method, detecting the presence of more of the one or more conjugate(s) in the lymphatics than a reference or control amount indicates the presence of cancer.

3. Treating

Also provided is a method of treating cancer in a subject. The method can involve administering to the subject a conjugate comprising any one or more of the herein disclosed peptides and one or more moieties. The one or more moieties can be therapeutic moieties. Thus, in some aspects, the conjugate inhibits lymphangiogenesis in a tumor in the subject. conjugate induces apoptosis of the tumor lymphatics. In some aspects, the conjugate induces apoptosis of the tumor.

The cancer of the disclosed method can be breast cancer. Thus, the polypeptide of the disclosed method can comprise the amino acid sequence XRTX (SEQ ID NO:59), where X is R or K (SEQ ID NOs:12-15); CGNKRTRGC (SEQ ID NO:16), CGNKRTRGC (SEQ ID NO:16) with one, two, three or four conservative amino acid substitutions, CGNKRTRGC (SEQ ID NO:16) with one, two or three non-conservative amino acid substitution, CGNKRTRGC (SEQ ID NO:16) with one, two or three non-conservative amino acid substitution and one, two, three or four conservative amino acid substitutions; CNKRTRGGC (SEQ ID NO:18), CNKRTRGGC (SEQ ID NO:18) with one, two, three or four conservative amino acid substitutions, CNKRTRGGC (SEQ ID NO:18) with one, two or three non-conservative amino acid substitution, or CNKRTRGGC (SEQ ID NO:18) with one, two or three non-conservative amino acid substitution and one, two, three or four conservative amino acid substitutions.

The cancer of the disclosed method can be cervical cancer. Thus, the polypeptide of the disclosed method can comprise the amino acid sequence XRTX (SEQ ID NO:59), where X is R or K (SEQ ID NOs:12-15); CNRRTKAGC (SEQ ID NO:17), CNRRTKAGC (SEQ ID NO:17) with one, two, three or four conservative amino acid substitutions, CNRRTKAGC (SEQ ID NO:17) with one, two or three non-conservative amino acid substitution, or CNRRTKAGC (SEQ ID NO:17) with one, two or three non-conservative amino acid substitution and one, two, three or four conservative amino acid substitutions.

The cancer of the disclosed method can be skin cancer. Thus, the polypeptide of the disclosed method can comprise the amino acid sequence CLSDGK (SEQ ID NO:2), CLSDGK (SEQ ID NO:2) with one, two or three conservative amino acid substitutions, CLSDGK (SEQ ID NO:2) with one non-conservative amino acid substitution, CLSDGK (SEQ ID NO:2) with one non-conservative amino acid substitution and one, two or three conservative amino acid substitutions; CLSDGKRKC (SEQ ID NO:4), CLSDGKRKC (SEQ ID NO:4) with one, two, three or four conservative amino acid substitutions, CLSDGKRKC (SEQ ID NO:4) with one, two or three non-conservative amino acid substitution, CLSDGKRKC (SEQ ID NO:4) with one, two or three non-conservative amino acid substitution and one, two, three or four conservative amino acid substitutions; CLSDGKPVS (SEQ ID NO:3), CLSDGKPVS (SEQ ID NO:3) with one, two, three or four conservative amino acid substitutions, CLSDGKPVS (SEQ ID NO:3) with one, two or three non-conservative amino acid substitution, CLSDGKPVS (SEQ ID NO:3) with one, two or three non-conservative amino acid substitution and one, two, three or four conservative amino acid substitutions; CLDGGRPKC (SEQ ID NO:5), CLDG- GRPKC (SEQ ID NO:5) with one, two, three or four conservative amino acid substitutions, CLDGGRPKC (SEQ ID NO:5) with one, two or three non-conservative amino acid substitution, or CLDGGRPKC (SEQ ID NO:5) with one, two or three non-conservative amino acid substitution and one, two, three or four conservative amino acid substitutions.

The cancer of the disclosed method can be prostate cancer. Thus, the polypeptide of the disclosed method can comprise the amino acid sequence CREAGRKAC (SEQ ID NO:6), CREAGRKAC (SEQ ID NO:6) with one, two, three or four conservative amino acid substitutions, CREAGRKAC (SEQ ID NO:6) with one, two or three non-conservative amino acid substitution, CREAGRKAC (SEQ ID NO:6) with one, two or three non-conservative amino acid substitution and one, two, three or four conservative amino acid substitutions; CSMSAKKKC (SEQ ID NO:7), CSMSAKKKC (SEQ ID NO:7) with one, two, three or four conservative amino acid substitutions, CSMSAKKKC (SEQ ID NO:7) with one, two or three non-conservative amino acid substitution, CSMSAKKKC (SEQ ID NO:7) with one, two or three non-conservative amino acid substitution and one, two, three or four conservative amino acid substitutions; CKTRVSCGV (SEQ ID NO:8), CKTRVSCGV (SEQ ID NO:8) with one, two, three or four conservative amino acid substitutions, CKTRVSCGV (SEQ ID NO:8) with one, two or three non-conservative amino acid substitution, CKTRVSCGV (SEQ ID NO:8) with one, two or three non-conservative amino acid substitution and one, two, three or four conservative amino acid substitutions; CAGRRSAYC (SEQ ID NO:9), CAGRRSAYC (SEQ ID NO:9) with one, two, three or four conservative amino acid substitutions, CAGRRSAYC (SEQ ID NO:9) with one, two or three non-conservative amino acid substitution, CAGRRSAYC (SEQ ID NO:9) with one, two or three non-conservative amino acid substitution and one, two, three or four conservative amino acid substitutions; CASLSCR (SEQ ID NO:10), CASLSCR (SEQ ID NO:10) with one, two or three conservative amino acid substitutions, CASLSCR (SEQ ID NO:10) with one or two non-conservative amino acid substitution, CASLSCR (SEQ ID NO:10) with one or two non-conservative amino acid substitution and one, two or three conservative amino acid substitutions; CSGGKVLDC (SEQ ID NO:11), CSGGKVLDC (SEQ ID NO:11) with one, two, three or four conservative amino acid substitutions, CSGGKVLDC (SEQ ID NO:11) with one, two or three non-conservative amino acid substitution, or CSGGKVLDC (SEQ ID NO:11) with one, two or three non-conservative amino acid substitution and one, two, three or four conservative amino acid substitutions.

The cancer of the disclosed method can be pre-malignant prostate cancer. Thus, the polypeptide of the disclosed method can comprise the amino acid sequence CAGRRSAYC (SEQ ID NO:9), CAGRRSAYC (SEQ ID NO:9) with one, two, three or four conservative amino acid substitutions, CAGRRSAYC (SEQ ID NO:9) with one, two or three non-conservative amino acid substitution, CAGRRSAYC (SEQ ID NO:9) with one, two or three non-conservative amino acid substitution and one, two, three or four conservative amino acid substitutions; CASLSCR (SEQ ID NO:10), CASLSCR (SEQ ID NO:10) with one, two or three conservative amino acid substitutions, CASLSCR (SEQ ID NO:10) with one or two non-conservative amino acid substitution, CASLSCR (SEQ ID NO:10) with one or two non-conservative amino acid substitution and one, two or three conservative amino acid substitutions; CSGGKVLDC (SEQ ID NO:11), CSGGKVLDC (SEQ ID NO:11) with one, two, three or four conservative amino acid substitutions, CSGGKVLDC (SEQ ID NO:11) with one, two or three non-conservative amino acid substitution, or CSGGKVLDC (SEQ ID NO:11) with one, two or three non-conservative amino acid substitution and one, two, three or four conservative amino acid substitutions.

The cancer of the disclosed method can be malignant prostate cancer. Thus, the polypeptide of the disclosed method can comprise the amino acid sequence CREAGRKAC (SEQ ID NO:6), CREAGRKAC (SEQ ID NO:6) with one, two, three or four conservative amino acid substitutions, CREAGRKAC (SEQ ID NO:6) with one, two or three non-conservative amino acid substitution, CREAGRKAC (SEQ ID NO:6) with one, two or three non-conservative amino acid substitution and one, two, three or four conservative amino acid substitutions; CSMSAKKKC (SEQ ID NO:7), CSMSAKKKC (SEQ ID NO:7) with one, two, three or four conservative amino acid substitutions, CSMSAKKKC (SEQ ID NO:7) with one, two or three non-conservative amino acid substitution, CSMSAKKKC (SEQ ID NO:7) with one, two or three non-conservative amino acid substitution and one, two, three or four conservative amino acid substitutions; CKTRVSCGV (SEQ ID NO:8), CKTRVSCGV (SEQ ID NO:8) with one, two, three or four conservative amino acid substitutions, CKTRVSCGV (SEQ ID NO:8) with one, two or three non-conservative amino acid substitution, CKTRVSCGV (SEQ ID NO:8) with one, two or three non-conservative amino acid substitution and one, two, three or four conservative amino acid substitutions.

The disclosed conjugates can be used to treat any disease where uncontrolled cellular proliferation occurs such as cancers. A non-limiting list of different types of cancers can be as follows: lymphomas (Hodgkins and non-Hodgkins), leukemias, carcinomas, carcinomas of solid tissues, squamous cell carcinomas, adenocarcinomas, sarcomas, gliomas, high grade gliomas, blastomas, neuroblastomas, plasmacytomas, histiocytomas, melanomas, adenomas, hypoxic tumors, myelomas, AIDS-related lymphomas or sarcomas, metastatic cancers, or cancers in general.

A representative but non-limiting list of cancers that the disclosed compositions can be used to treat is the following: lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, and epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, or pancreatic cancer.

4. Diagnosing

Also provided is a method of determining normal, pre-malignant and malignant prostate conditions in a subject. The method can involve contacting a biological sample from the subject with a conjugate disclosed herein, wherein the polypeptide comprises the amino acid sequence CREAGRKAC (SEQ ID NO:6), CREAGRKAC (SEQ ID NO:6) with one, two, three or four conservative amino acid substitutions, CREAGRKAC (SEQ ID NO:6) with one, two or three non-conservative amino acid substitution, CREAGRKAC (SEQ ID NO:6) with one, two or three non-conservative amino acid substitution and one, two, three or four conservative amino acid substitutions; CSMSAKKKC (SEQ ID NO:7), CSMSAKKKC (SEQ ID NO:7) with one, two, three or four conservative amino acid substitutions, CSMSAKKKC (SEQ ID NO:7) with one, two or three non-conservative amino acid substitution, CSMSAKKKC (SEQ ID NO:7) with one, two or three non-conservative amino acid substitution and one, two, three or four conservative amino acid substitutions; CKTRVSCGV (SEQ ID NO:8), CKTRVSCGV (SEQ ID NO:8) with one, two, three or four conservative amino acid substitutions, CKTRVSCGV (SEQ ID NO:8) with one, two or three non-conservative amino acid substitution, CKTRVSCGV (SEQ ID NO:8) with one, two or three non-conservative amino acid substitution and one, two, three or four conservative amino acid substitutions; CAGRRSAYC (SEQ ID NO:9), CAGRRSAYC (SEQ ID NO:9) with one, two, three or four conservative amino acid substitutions, CAGRRSAYC (SEQ ID NO:9) with one, two or three non-conservative amino acid substitution, CAGRRSAYC (SEQ ID NO:9) with one, two or three non-conservative amino acid substitution and one, two, three or four conservative amino acid substitutions; CASLSCR (SEQ ID NO:10), CASLSCR (SEQ ID NO:10) with one, two or three conservative amino acid substitutions, CASLSCR (SEQ ID NO:10) with one or two non-conservative amino acid substitution, CASLSCR (SEQ ID NO:10) with one or two non-conservative amino acid substitution and one, two or three conservative amino acid substitutions; CSGGKVLDC (SEQ ID NO:11), CSGGKVLDC (SEQ ID NO:11) with one, two, three or four conservative amino acid substitutions, CSGGKVLDC (SEQ ID NO:11) with one, two or three non-conservative amino acid substitution, or CSGGKVLDC (SEQ ID NO:11) with one, two or three non-conservative amino acid substitution and one, two, three or four conservative amino acid substitutions.

In some aspects of the disclosed method, selective binding of CAGRRSAYC (SEQ ID NO:9), CAGRRSAYC (SEQ ID NO:9) with one, two, three or four conservative amino acid substitutions, CAGRRSAYC (SEQ ID NO:9) with one, two or three non-conservative amino acid substitution, CAGRRSAYC (SEQ ID NO:9) with one, two or three non-conservative amino acid substitution and one, two, three or four conservative amino acid substitutions; CASLSCR (SEQ ID NO:10), CASLSCR (SEQ ID NO:10) with one, two or three conservative amino acid substitutions, CASLSCR (SEQ ID NO:10) with one or two non-conservative amino acid substitution, CASLSCR (SEQ ID NO:10) with one or two non-conservative amino acid substitution and one, two or three conservative amino acid substitutions; or CSGGKVLDC (SEQ ID NO:11), CSGGKVLDC (SEQ ID NO:11) with one, two, three or four conservative amino acid substitutions, CSGGKVLDC (SEQ ID NO:11) with one, two or three non-conservative amino acid substitution, or CSGGKVLDC (SEQ ID NO:11) with one, two or three non-conservative amino acid substitution and one, two, three or four conservative amino acid substitutions is an indication of a pre-malignant prostate condition.

In some aspects of the disclosed method, selective binding of CREAGRKAC (SEQ ID NO:6), CREAGRKAC (SEQ ID NO:6) with one, two, three or four conservative amino acid substitutions, CREAGRKAC (SEQ ID NO:6) with one, two or three non-conservative amino acid substitution, CREAGRKAC (SEQ ID NO:6) with one, two or three non-conservative amino acid substitution and one, two, three or four conservative amino acid substitutions; CSMSAKKKC (SEQ ID NO:7), CSMSAKKKC (SEQ ID NO:7) with one, two, three or four conservative amino acid substitutions, CSMSAKKKC (SEQ ID NO:7) with one, two or three non-conservative amino acid substitution, CSMSAKKKC (SEQ ID NO:7) with one, two or three non-conservative amino acid substitution and one, two, three or four conservative amino acid substitutions; or CKTRVSCGV (SEQ ID NO:8), CKTRVSCGV (SEQ ID NO:8) with one, two, three or four conservative amino acid substitutions, CKTRVSCGV (SEQ ID NO:8) with one, two or three non-conservative amino acid substitution, CKTRVSCGV (SEQ ID NO:8) with one, two or three non-conservative amino acid substitution and one, two, three or four conservative amino acid substitutions is an indication of a malignant prostate condition.

In some aspects of the disclosed method, a lack of selective binding of CAGRRSAYC (SEQ ID NO:9), CAGRRSAYC (SEQ ID NO:9) with one, two, three or four conservative amino acid substitutions, CAGRRSAYC (SEQ ID NO:9) with one, two or three non-conservative amino acid substitution, CAGRRSAYC (SEQ ID NO:9) with one, two or three non-conservative amino acid substitution and one, two, three or four conservative amino acid substitutions; CASLSCR (SEQ ID NO:10), CASLSCR (SEQ ID NO:10) with one, two or three conservative amino acid substitutions, CASLSCR (SEQ ID NO:10) with one or two non-conservative amino acid substitution, CASLSCR (SEQ ID NO:10) with one or two non-conservative amino acid substitution and one, two or three conservative amino acid substitutions; or CSGGKVLDC (SEQ ID NO:8), CREAGRKAC (SEQ ID NO:3), CSMSAKKKC (SEQ ID NO:4), or CSGGKVLDC (SEQ ID NO:11), CSGGKVLDC (SEQ ID NO:11) with one, two, three or four conservative amino acid substitutions, CSGGKVLDC (SEQ ID NO:11) with one, two or three non-conservative amino acid substitution, or CSGGKVLDC (SEQ ID NO:11) with one, two or three non-conservative amino acid substitution and one, two, three or four conservative amino acid substitutions, is an indication of a normal prostate condition.

5. Screening

Also provided is a method of identifying an agent that targets tumor lymphatics. The method can involve, for example,
(a) contacting non-cancerous tissue with a library of candidate agents under conditions sufficient to allow for selective binding of agents to the non-cancerous tissue,
(b) collecting candidate agents that do not bind non-cancerous tissue from step (a),
(c) contacting cancerous or pre-malignant tissue with the candidate agents collected in step (b) under conditions sufficient to allow for selective binding of agents to the cancerous or pre-malignant tissue, and
(d) collecting candidate agents bound to lymphatic endothelial cells from the cancerous or pre-malignant tissue, wherein binding of candidate agents to lymphatic endothelial cells to the cancerous or pre-malignant tissue identifies the candidate agent as an agent that targets tumor lymphatics.

For example, the library of candidate agents can be from a phage library.

The disclosed method can further comprise producing the candidate agent identified as an agent that targets tumor lymphatics.

6. Administration

A composition disclosed herein, such as the disclosed peptides and conjugates, may be administered in a number of ways depending on whether local or systemic treatment is desired, and on the area to be treated. For example, the compositions may be administered orally, parenterally (e.g., intravenous, subcutaneous, intraperitoneal, or intramuscular injection), by inhalation, extracorporeally, topically (including transdermally, ophthalmically, vaginally, rectally, intranasally) or the like.

As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. Thus, effective dosages and schedules for administering the compositions may be determined empirically, and making such determinations is within the skill in the art. Useful dosage ranges for the administration of the compositions are those large enough to produce the desired effect. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products.

For example, a typical daily dosage of the disclosed peptides used alone might range from about 1 µg/kg to up to 100 mg/kg of body weight or more per day, depending on the factors mentioned above.

Following administration of a disclosed composition, the efficacy of a therapeutic moiety can be assessed in various ways well known to the skilled practitioner. For instance, one of ordinary skill in the art will understand that a composition disclosed herein is efficacious in treating or inhibiting cancer in a subject by observing that the composition reduces tumor growth or prevents a further increase in lymphangiogenesis.

C. Kits

The materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing conjugates, such as those disclosed herein, the kit comprising a peptide and a means for linking the peptide to a moiety. The kits also can contain protocols for preparing the conjugate.

D. Uses

The disclosed compositions can be used in a variety of ways as research tools. Other uses are disclosed, apparent from the disclosure, and/or will be understood by those in the art.

E. Methods of Making the Compositions

The compositions disclosed herein and the compositions necessary to perform the disclosed methods can be made using any method known to those of skill in the art for that particular reagent or compound unless otherwise specifically noted.

1. Nucleic Acid Synthesis

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

2. Peptide Synthesis

One method of producing the disclosed proteins is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide-thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269: 16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, Metal. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

F. Definitions

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents.

It must be noted that as used herein and in the appended claims, the singular forms "a," "an," and "the" include plural reference unless the context clearly dictates otherwise. Thus, for example, reference to "a peptide" includes a plurality of such peptides, reference to "the peptide" is a reference to one or more peptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is, expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Throughout the description and claims of this specification, the word "comprise" and variations of the word, such as "comprising" and "comprises," means "including but not limited to," and is not intended to exclude, for example, other additives, components, integers or steps.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

The terms "targeting" or "homing", as used herein can refer to the preferential movement, binding and/or accumulation of a targeted compound or composition, such as the disclosed compositions, at a site or a location as compared to a non-targeted compound or composition. For example, in the context of in vivo administration to a subject, "targeting" or "homing" can refer to the preferential movement, binding, and/or accumulation of a compound or composition, such as the disclosed compositions, in or at, for example, target tissue, target cells, and/or target structures as compared to non-target tissue, cells and/or structures.

The term "target tissue" as used herein refers to an intended site for accumulation of a targeted compound or composition, such as the disclosed compositions, following administration to a subject. For example, the methods of the presently disclosed subject matter employ a target tissue comprising endometriosis.

As used herein, "subject" includes, but is not limited to, animals, plants, bacteria, viruses, parasites and any other organism or entity that has nucleic acid. The subject may be a vertebrate, more specifically a mammal (e.g., a human, horse, pig, rabbit, dog, sheep, goat, non-human primate, cow, cat, guinea pig or rodent), a fish, a bird or a reptile or an amphibian. The subject may to an invertebrate, more specifically an arthropod (e.g., insects and crustaceans). The term does not denote a particular age or sex. Thus, adult and newborn subjects, as well as fetuses, whether male or female, are intended to be covered. A patient refers to a subject afflicted with a disease or disorder. The term "patient" includes human and veterinary subjects. In the context of endometriosis and endometriosis cells, it is understood that a subject is a subject that has or can have endometriosis and/or endometriosis cells.

By "treatment" is meant the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

G. Examples

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1 i. Experimental Procedures

Cell Lines, Mice, and Tumors:

The following cell lines were maintained in DMEM supplemented with 10% FCS: C8161 human melanoma, MDA-MB-435 human breast cancer, KRIB human osteosarcoma, and human prostate cancer cells PPC1, DU145. LNCaP human prostate cancer cell line was grown in RPMI 1640 medium with 10 mM HEPES, 1 mM sodium pyruvate and 1.5 g/L sodium bicarbonate supplemented with 10% FCS. M12 human prostate cancer cell line was cultured in RPMI 1640 with 5 µg/ml insulin-transferrin-sodium selenite (ITS), 2.5 µg/ml fungizone, 50 µg/ml gentamycin, 0.2 µM dexamethasone, 10 ng/ml epidermal growth factor (EGF), and 5% FCS (Bae et al., 1998). To produce tumors, nude BALB/c and C56BL/6 mice were subcutaneously (C8161, KRIB, and PPC1) or orthotopically (MDA-MB-453, PPC1, DU145, M12, and LNCaP) injected with 1×106 tumor cells. Transgenic mouse tumor models included TRAMP prostate cancer, MMTV-PyMT breast cancer, and K14-HPV16 cervical cancer. To initiate cervical carcinogenesis, female K14-HPV16 mice (Arbeit et al., 1994) were treated with 17β-estradiol (E2; (Arbeit et al., 1996; Giraudo et al., 2004). Briefly, one-month-old virgin female transgenic (heterozygous K14-HPV16, 1203#1) and nontransgenic (FVB/n) mice were anesthetized with isoflurane, and continuous release pellets that deliver E2 at doses of 0.05 mg over 60 days (Innovative Research of America, Sarasota, Fla., USA) were implanted subcutaneously in the dorsal back skin. Subsequent pellets were implanted at 3 and 5 months of age for a total of 6 months of hormone treatment. K14-HPV16 mice were maintained in the FVB/n background (FVB/n; The Jackson Laboratory). The mice were maintained in accordance with the University of California, San Francisco (UCSF) institutional guidelines governing the care of laboratory mice. The animal experimentation was approved by Animal Research Committees at UCSF or The Burnham Institute.

Phage Library and Screening:

An NNK-encoded CX7C library display on T7Select415-1 phage (Novagen) was prepared as previously described (Laakkonen et al., 2002). Phage selection and validation have been described (Hoffman, 2004). A two-step procedure was designed for the selection of peptides targeting the tumor lymphatic vessels of pre-malignant prostate lesions and prostate tumor. First, the phage library was incubated with cells derived from normal prostate to subtract the phage that bind to normal prostate. Second, the anti-podoplanin magnetic beads were used to isolate lymphatic endothelial cells. 2-3 rounds of ex vivo selection and 2-3 rounds of in vivo selections were performed. For the ex vivo selections, cell suspensions were prepared from normal prostates of tumor-free littermates of TRAMP mice, pre-malignant prostates of 14- to 16-week-old TRAMP mice, and tumor tissues of 25- to 28-week-old TRAMP mice. Collagenase IA (1 mg/ml, Sigma) was used to disperse the tissues. About $1 \times 10^7$ normal prostate cells were incubated at 4° C. for 3 hrs with $5 \times 1010$ plaque forming units (pfu) of T7 phage displaying a CX7C peptide library. The samples were centrifuged at 1200 rpm for 10 min, the supernatant (the normal prostate-subtracted phage library) was recovered and then incubated overnight at 4° C. with $5 \times 10^7$ cells derived from pre-malignant prostate tissue or prostate tumor. The cells were washed to remove unbound phage, incubated with rat anti-mouse podoplanin for 45 min at 4° C., and washed three times with cold PBS containing 0.5% BSA. Podoplanin-positive cells were then isolated using M450 sheep anti-rat IgG Dynabeads (M450; Dynal, Oslo, Norway). Phage that bound to the podoplanin-positive cell population were rescued and amplified in E. coli. In vivo phage library screening was performed as described (Laakkonen et al., 2002).

Homing Specificity of Phage:

In vivo homing specificity of phage was tested as described (Hoffman, 2004). Briefly, mice bearing tumors were anesthetized and intravenously injected with $5 \times 10^9$ pfu of phage. After 7 min, the mice were perfused through the heart with PBS containing 0.5% BSA. The tumor and control organs were dissected from each mouse and the phage were rescued and tittered. For histology analysis, the mice were perfused with 4% PFA 30 min after the injection of phage. Tissues were embedded in Tissue-Tek O.C.T. and 5 µm sections were prepared for phage immunostaining.

Antibodies and Immunohistology:

Custom immunization to produce a rabbit antiserum against mouse Prox-1 was performed by Proteintech Inc. New Zealand White rabbits were immunized with a fusion protein of GST-C-terminal fragment of Prox-1 protein. The antibody was affinity purified on the fusion protein and absorbed with GST. The resulting antibody preparation (1.8 mg/ml) gave a titer of 1:10,000 against the fusion protein in ELISA. Immunofluorescence staining of tissue sections with the anti-Prox-1 antibody gave a pattern of nuclear staining. Antibodies against the lymphatic markers anti-LYVE-1 (Laakkonen et al., 2002) and anti-podoplanin (kindly provided by T. Petrova and K. Alitalo), rat monoclonal anti-mouse CD31 (BD Pharmingen), rat anti-mouse MECA-32 (Pharmingen), rabbit polyclonal anti-T7 phage, and rat anti-mouse VEGFR3 were used for immunohistochemical staining of frozen tissue sections as described (Joyce et al., 2003; Laakkonen et al., 2002). The corresponding secondary antibodies were added and incubated for 1 hr at room temperature: AlexaFluor-488 goat anti-rat or rabbit IgG (1:1000; Molecular Probes, Eugene, Oreg.), AlexaFluor-594 goat anti-rat or rabbit IgG (1:1000, Molecular Probes), AlexaFluor-594 donkey anti-mouse or goat IgG (1:1000, Molecular Probes), and AlexaFluor-488 donkey anti-mouse or goat IgG (1:1000; Molecular Probes), respectively. The slides were washed three times with PBS and mounted in Vectashield Mounting Medium with DAPI (Vector Laboratories, Burlingame, Calif.). Blood vessels were also visualized by intravenously injecting *Lycopersicon esculentum* (tomato) lectin conjugated to fluorescein (100 µg of lectin in 200 µl of PBS; Vector Laboratories). Tissue distribution of fluorescein-labeled peptides (Laakkonen et al., 2004) was studied by intravenously injecting the peptide (100-150 µg in 200 µl PBS) into the mice. The injected peptides were allowed to circulate 30 min to 2 hrs, and the mice were perfused with 4% paraformaldehyde through the left ventricle of heart. Tissues were dissected and frozen in OCT embedding medium (Tissue-Tek, Elkhart, Ind.). The frozen sections were prepared for immunohistological analysis.

Peptide Synthesis:

Peptides were synthesized using Fmoc chemistry in a solid-phase synthesizer. The peptides were purified by HPLC and confirmed by mass spectrometry. Fluorescein-conjugated peptides were synthesized as described (Laakkonen et al., 2004). The LSD peptide and REA peptide were synthesized as the chimera with the pro-apoptotic motif $_D$(KLAKLAK)$_2$ (SEQ ID NO:19; Ellerby et al., 1999).

Transfection and Phage Binding Assay:

The 293T cells were transfected with plasmids encoding CXCR4 (Helbig et al., 2003) or VEGFR2 (Borges et al., 2000) using FuGene 6 transfection reagent (Roche Diagnostics, Indianapolis, Ind.). Briefly, plasmid (10 µg) was mixed with 900 µl of serumfree DMEM and 50 µl of FuGene and incubated for 15 min at room temperature before adding the mixture to the cells. The cells were detached using EDTA after 48 hrs post transfection and washed with PBS containing 1% BSA. Phage (5×10$^9$ pfu) were incubated with the transfected cells and bound phage were rescued and titrated. For competitive binding assay, the cognate peptide (150 µg/ml) or antibody (50 µg/ml) was added during incubating of the phage with cells. Targeted proapoptotic peptide treatment of tumor-bearing mice Prostate cancer model. Orthotopic xenografted prostate tumors were established by injecting 1×10$^6$ PPC1 human prostate cancer cells into the mouse prostate. Fifteen days post inoculation, the mice were intravenously injected with $_D$(KLAKLAK)$_2$-CREAGRKAC (SEQ ID NO:41), an equimolar mixture of $_D$(KLAKLAK)$_2$ (SEQ ID NO:19) and CREAGRKAC (SEQ ID NO:6), or PBS. Biweekly injections of 100 µg/dose/mouse were given for three weeks. Melanoma model. Nude BALB/c mice were subcutaneously injected with 1×10$^6$ C8161 human melanoma cells. Treatment started when mean tumor volumes reached about 100 mm3. Mice with size-matched tumors were randomized into three groups. The therapeutic group received a chimera of tumor homing peptide with the proapoptotic motif ($_D$(KLAKLAK)$_2$-CLSDCGKRKC; SEQ ID NO:42). The control groups received an equimolar mixture of CLS-DGKRKC (SEQ ID NO:4) and $_D$(KLAKLAK)$_2$ (SEQ ID NO:19), or PBS alone. The tumor-bearing mice were intravenously injected with 200 µg/dose/mouse once a week for three weeks. The mice were monitored for weight loss, and tumors were dissected and weighed at the termination of the experiment. Histological analysis was performed to evaluate the density of tumor lymphatics and blood vessels. The animal experiments reported here were approved by The Burnham Institute Animal Research Committee.

Phage Overlay of Tissue Sections from Human Cancer:

The frozen sections of human prostate tumor specimens were obtained from Dr. Daniel Mercola (Sidney Kimmel Cancer Center, La Jolla, Calif.). The sections (5 µm) were preincubated with blocking buffer (5% normal goat serum and 0.5% BSA in 1×PBS) for 1 hr at room temperature, washed three times with diluted blocking buffer (1:10), and phage (3×10$^9$ pfu) were incubated on the section for 4 hrs. After 3 washes, rabbit anti-phage antibody (10 µg/ml) was added and the phage incubated for 2 hrs. The slides were washed and incubated with AlexaFluor-488 goat anti-rabbit IgG for 1 hr. After further washes, the slides were mounted with Vectashield (VECTOR, Burlingame, Calif.).

Statistical Analysis:

Student's t test was used in statistical analysis of the results. The bar diagrams show mean and standard deviation.

ii. Results

Phage Targeting of Lymphatics in C8161 Melanoma:

The C8161 human melanoma was chosen as the first target because xenografts of tumors generated with this cell line in nude mice contain lymphatic vessels that are not recognized by the homing peptide, LyP-1, which binds to lymphatic endothelial cells in breast carcinomas (Laakkonen et al., 2002). The experimental design was aimed to determine whether lymphatic homing peptides having analogous specificity for the melanoma-associated lymphatics could be identified. protocols were modified to increase the probability of obtaining peptides that recognize tumor lymphatics. A phage display library was incubated with a cell suspension of whole C8161 tumor tissue, allowing phage to bind, and then used immuno-magnetic beads to isolate lymphatic endothelial cells that carried along any phage bound to these cells. This enrichment step yielded a phage pool that bound 250-fold more efficiently to the isolated cells than nonrecombinant phage (FIG. 9A). The enriched phage pool was used in subsequent in vivo rounds to select phage that homed to C8161 xenograft tumors. Two rounds of selection in vivo produced a 40-fold enrichment of phage (FIG. 9B). There was no enrichment in the several control organs tested.

The 48 phage clones from the second in vivo round of phage pool selection included five clones that appeared most frequently, and these were analyzed further. Two clones displaying peptides with related amino acid sequences CLSDGKRKC (SEQ ID NO:4) and CLDGGRPKC (SEQ ID NO:5) bound to cell suspensions prepared from C8161 tumors; the stronger binder, CLSDGKRKC (SEQ ID NO:4), bound 100 fold more than control phage. Intravenous injection of phage into nude mice bearing C8161 tumors showed that both phage homed selectively to the tumors; CLSDGKRKC (SEQ ID NO:4) was about twice as efficient as CLDGGRPKC (SEQ ID NO:5) (the results for CLSDGKRKC (SEQ ID NO:4) are shown in FIG. 1A). The CLS- DGKRKC (SEQ ID NO:4) peptide (referred to below as LSD) was chosen for further study. To establish that the homing ability of LSD phage is due to the displayed peptide sequence, the peptide was chemically synthesized as a fluorescein-conjugate peptide and intravenously injected the conjugate into C8161 tumor mice. After 2 hrs of circulation, the peptide was detected within the tumors, but not in control organs. Staining of tissue sections with the lymphatic vessel markers podoplanin, Prox-1, LYVE-1, and VEGFR3, showed co-localization of the LSD fluorescence with them (FIG. 1C), whereas there was no co-localization with the blood vessel markers MECA-32 and CD31. Quantification showed that 85% of the lymphatic vessels that were positive for the peptide were also positive for podoplanin.

The homing of LSD phage to other types of cancer was further tested, including the MDA-MB-435 human breast cancer xenografts recognized by the previously described lymphatic homing peptide, LyP-1 (Laakkonen et al., 2002). Intravenously injected LSD phage did not appreciably home to MDA-MB-435 tumors (see below). These data show that LSD-peptide selectively homes to the lymphatic vessels in C8161 melanoma.

FITC-LSD (150 mg) was intravenously injected into tumor mice and allowed to circulate for 2 hrs. The tumor and various tissues were collected and processed for histological analysis. A few spots of LSD fluorescence were seen in the kidneys; all other tissues, with the exception of the tumors (FIG. 1B-D), were negative.

Phage Targeting of Lymphatics in Pre-Malignant Lesions and Tumors of Prostate:

Seeking to further generalize the proposition that tumor-associated lymphatics might have organ specific signatures, lymphatic homing peptides were selected in the TRAMP transgenic mouse model of de novo prostate carcinogenesis (Hsu et al., 1998). Immunohistochemical analysis had revealed abundant lymphatics associated both with pre-malignant lesions and tumors in this model. As it is possible to access pre-malignant lesions in this system, the possibility of distinguishing the lymphatics of such lesions from those of fully developed tumors was also explored.

To isolate peptides that selectively home to fully developed tumors in the TRAMP model, the phage library were first pre-treated with cell suspensions derived from normal prostate to decrease the abundance of phage that bind to normal prostate. The normal prostate-subtracted library was then enriched by two rounds of ex vivo selection on lymphatic endothelial cells immuno-purified from tumors of 25- to 28-week-old TRAMP mice. Three subsequent in vivo selection rounds yielded a phage pool that showed nearly 50-fold enrichment for tumor homing. Five peptide sequences were represented more than once in this pool. Three of these phage clones with amino acid sequences CREAGRKAC (SEQ ID NO:6), CSMSAKKKC (SEQ ID NO:7), and CKTRVSCGV (SEQ ID NO:8) showed robust binding to tumor derived cell suspensions and were further tested in vivo. Intravenously injected CREAGRKAC (SEQ ID NO:6) phage became 50-fold enriched in TRAMP tumors relative to nonrecombinant phage, while the other two phage showed about 30-fold enrichment. CREAGRKAC (REA; SEQ ID NO:6) was chosen for further study.

To screen for peptides recognizing the pre-malignant lymphatics, the phage library was first treated with cell suspensions derived from normal prostate, and the subtracted library was then enriched on immuno-purified lymphatic endothelial cell suspensions derived from prostates containing pre-malignant lesions (14- to 16-week-old mice). The sequential ex vivo selections yielded a phage pool that was 60-fold enriched for binding to the target cells, and 30-fold enrichment for homing to prostate with pre-malignant lesions was obtained in a subsequent in vivo selection. Five phage clones were chosen for evaluation of in vivo homing based on their frequent appearance among 64 clones sequenced (32 clones each from the second ex vivo round and the third in vivo round).

Of these, three clones with amino acid sequences CAGRRSAYC (SEQ ID NO:9), CASLSCR (SEQ ID NO:10), CSGGKVLDC (SEQ ID NO:11), bound to cell suspension derived from pre-malignant prostate lesions. These candidates were further tested in vivo individually. Phage displayed peptides CAGRRSAYC (SEQ ID NO:9), CSGGKVLDC (SEQ ID NO:11), and CASLSCR (SEQ ID NO:10) showed 24-, 14-, and 12-fold enrichment to pre-malignant TRAMP lesions relative to nonrecombinant phage, respectively. CAGRRSAYC (AGR; SEQ ID NO:9) was chosen for further study.

Figure 2A:
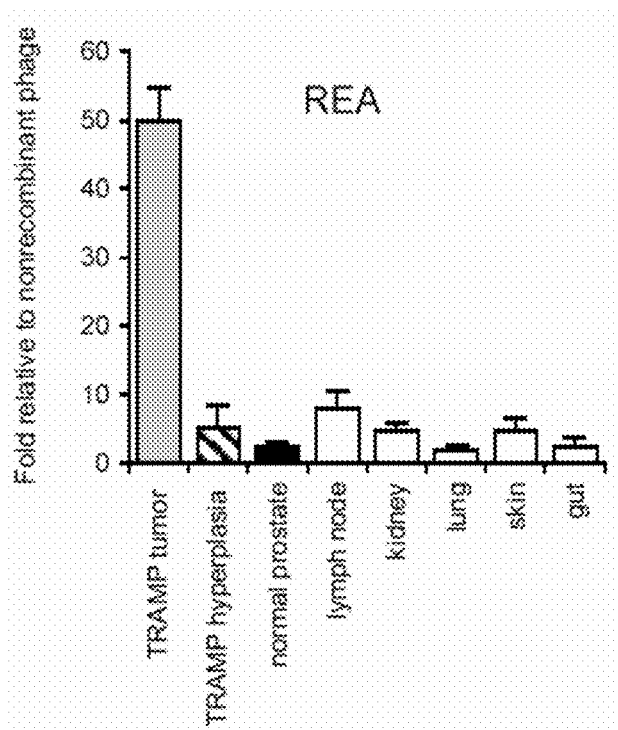
FIGS. 2A and 2B show stage-specific peptides distinguish pre-malignant lesions and tumors in the prostate of TRAMP mice and colocalize with lymphatic vessels. Phage isolated by screening for homing to TRAMP tumors (REA) or to TRAMP pre-malignant lesions (AGR) were individually tested in TRAMP mice bearing tumors, or pre-malignant lesions, and in tumor-free littermates of TRAMP mice with normal prostate. TRAMP mice were intravenously injected with phage or fluorescein-conjugated peptides, and the localization of the phage was studied by phage titration or immunohistochemistry in frozen tissue sections. The peptides were detected in tissue sections by examining fluorescence. The REA-phage (A) accumulate in TRAMP tumors, whereas the AGR phage (B) selectively home to pre-malignant lesions. The difference between tumor tissue and pre-malignant tissue was significant for both peptides (P<0.01; n=3 to 6) Original magnification: 400×.
Figure 2B:
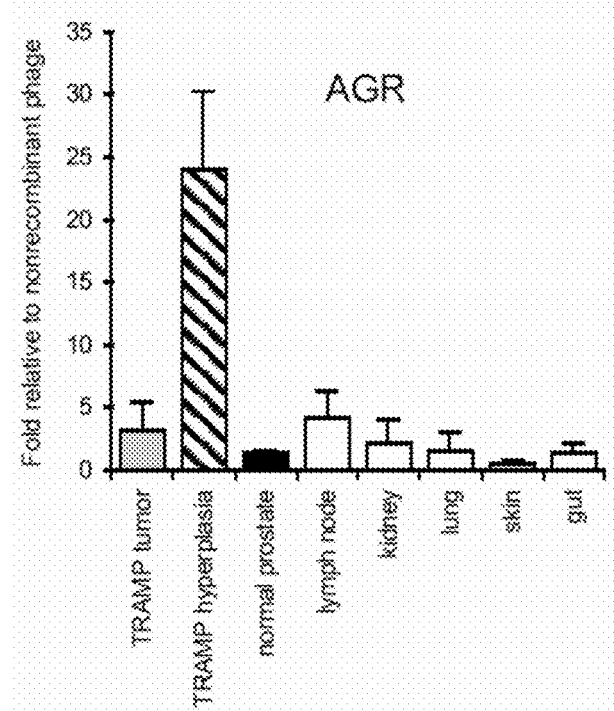

To evaluate the specificity of the REA and AGR peptides, the phage were intravenously injected into TRAMP mice with either pre-malignant lesions or tumors, or into their tumor-free (transgene negative) male littermates with normal prostates. The results showed that the REA phage homes to tumors, but not to pre-malignant lesions or normal prostate (FIG. 2A), whereas the AGR phage homes only to pre-malignant lesions (FIG. 2B). Neither phage was found in other tissues, including lymph nodes, kidneys, lungs, skin, or gut, at levels higher than the nonrecombinant control phage.

In vivo distribution of fluorescein-conjugated REA and ARG peptides after intravenous injection confirmed the phage results. The REA peptide accumulated in prostate tumors, showing 90% overlap with podoplanin-positive lymphatic vessels, whereas premalignant lesions, normal prostate, or control organs were negative. The AGR peptide selectively homed to pre-malignant TRAMP lesions, but little or no peptide was seen in prostate tumors, normal prostate tissue, or in control tissues.

Specifically, pre-malignant prostate tissue and tumor tissue were obtained from TRAMP mice at the ages of 14-16 and 25-28 weeks, respectively. Lymphatics were visualized by staining frozen sections with rabbit anti-mouse LYVE-1 and blood vessels were stained with rat anti-mouse MECA-32. The fluorescein-labeled REA peptide (150 µg) was intravenously injected into TRAMP tumor mice and the tumors and various control tissues were collected for histological analysis 2 hrs later. No FITC-REA was detected in the skin, lungs, gut, or brain. The liver and kidneys contained fluorescence at levels far lower than the TRAMP tumors. The fluorescein-labeled AGR peptide (150 µg) was intravenously injected into 14- to 16-week-old TRAMP mice and the tumors and various control tissues were collected for histological analysis 2 hrs later. No FITC-AGR was detected in the skin, lungs, gut, brain, or heart. The kidneys contained fluorescence at levels far lower than the pre-malignant lesions.

To study the association of REA and ARG peptides with the vasculature, the phage or the fluorescein-labeled peptides were intravenously injected into TRAMP mice, and phage and peptide localization was compared to lymphatic and blood vessel markers localized with antibodies. The phage and their cognate peptides each showed substantial co-localization with the lymphatic markers podoplanin, VEGFR3, LYVE-1, and Prox-1 in their respective lesions, whereas their localization was entirely distinct from that of the blood vessel markers CD31 and MECA-32.

Homing Peptide for Lymphatic Vessels in Cervical Cancer:
A homing peptide for dysplastic skin lesions has been identified in K14-HPV16 transgenic mice, which develop skin cancers (Hoffman et al., 2003). This peptide, CNRRTKAGC (SEQ ID NO:17), is similar to LyP-1 (CGNKRTRGC; SEQ ID NO:16), which selectively recognizes lymphatic vessels and tumor cells in breast cancers (Laakkonen et al., 2002). Because of this similarity, it was asked whether the CNRRTKAGC peptide (LyP-2; SEQ ID NO:17) also recognizes tumor lymphatics. The LyP-1 and LyP-2 peptides were tested in skin and cervical cancers of the K14-HPV16 mice. In addition to their spontaneously developing skin cancers, female K14-HPV16 mice develop cervical cancers when treated with estrogen (Arbeit et al., 1996). These mice (K14-HPV16/E2 mice) develop tumors in both organs through steps of neoplastic progression in a fashion that mimics the human cancers (Arbeit et al., 1996; Coussens et al., 1996; Giraudo et al., 2004). The pre-malignant cervical lesions (also called cervical intraepithelial neoplasia, CIN) and tumors of these mice contain abundant lymphatic vessels as detected by immunostaining for lymphatic markers.

LYVE-1 positive structures were seen in both the carcinoma and CIN-3 lesion. Similar results were obtained with another lymphatic marker, Prox-1. Original magnification: 100×; inset, 400×. FIG. 11B shows fluorescein labeled-LyP-2 peptide homes to cervical carcinoma in K14-HPV16/E2 mice. FITC-LyP-2 peptide (100 μg) was injected intravenously into tumor-bearing mice, and tissues were processed for histological analysis 2 hrs later. Little or no fluorescence was seen in normal cervix, skin, liver, or brain.

Figure 3:
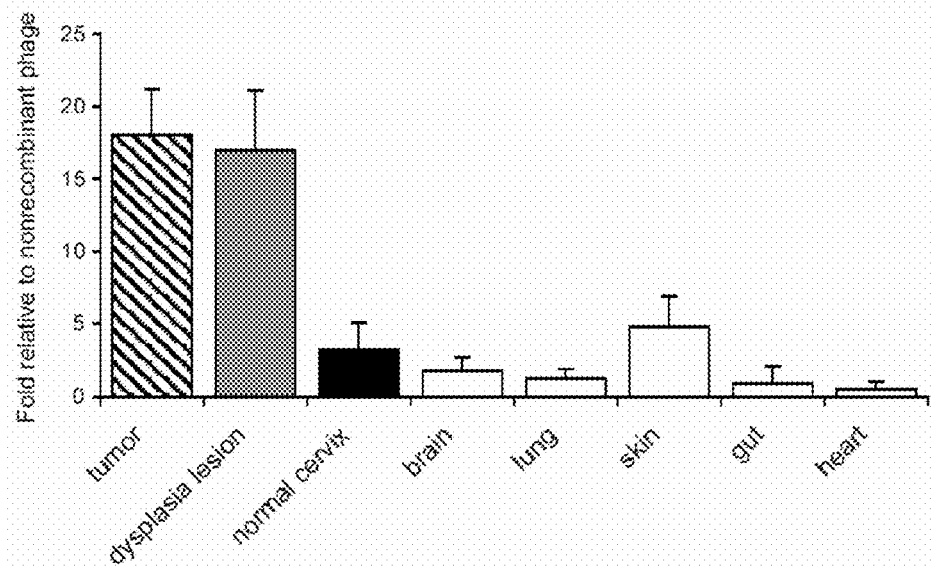
FIG. 3 shows LyP-2 peptide homes to lymphatics in pre-malignant lesions and tumors of cervix in K14-HPV16/E2 transgenic mice. LyP-2 phage ($1.5 \times 10^9$ pfu) was intravenously injected into mice bearing CIN-3 lesions or tumors of the cervix and phage titers from the indicated tissues were determined. Significantly more of the LyP-2 phage accumulated in the tumors and dysplastic lesions than in normal cervix (P<0.005; n=3).

Intravenously injected LyP-2 phage showed robust homing both to the pre-malignant and malignant lesions in the cervix, but not to normal cervix (FIG. 3). Fluoresceinlabeled LyP-2 peptide also accumulated in the cervical lesions, co-localizing with LYVE-1 and podoplanin (82% overlap), but not with MECA-32. Additionally, occasional foci of scattered cells in the stroma were labeled, with some apparent intracellular localization; the identity of these cells is currently unresolved. No peptide accumulation was observed in normal cervix or in other control tissues, either in lymphatics or in non-vascular cells (FIG. 11B). LyP-2 also homed to the lymphatics associated with dysplasias and squamous cell carcinomas in the skin in male and female mice, but not to normal skin lymphatics.

Specificity of Lymphatic Homing-Peptides for Different Types of Tumors:

Having isolated phage-displayed peptides that homed to the lymphatics of melanoma, prostate, or cervix, it was asked whether they recognized common determinants of the tumor-associated lymphatic vasculature or organ/tumor selective signatures. The origin and specificity of these peptides is shown in Table 3. The lymphatic homing peptides derived from the different tumor models were tested for their ability to recognize the lymphatics of other tumors. Intravenously injected LSD phage did not home to xenotransplant tumors derived from the MDA-MB-435 breast tumor cell line (FIG. 4). This phage also did not appreciably home to transgenic mouse tumors of the breast or prostate, or to PPC1 human prostate cancer xenografts; possible low-level homing was seen to transgenic skin cancers and KRIB human osteosarcoma xenografts. In vivo injection of fluorescein-labeled LSD peptide followed by histological analysis of peptide distribution agreed well with the phage results. Strong LSD peptide fluorescence was seen in the C8161 derived tumors, the model in which the peptide was selected. The C8161 tumors were positive in nude mice representing two different genetic backgrounds (BALB/c and C57BL/6). In agreement with the phage data, KRIB tumors were weakly positive with the fluorescent peptide, and the other tumors, including the skin cancers, were negative. These results show that the LSD peptide selectively recognizes the lymphatics in the C8161 melanoma-derived tumors.

TABLE 3

Main characteristics of lymphatic homing peptides

| Peptide | Tumor used to isolate homing peptide | Tumors tested for phage homing in vivo* | Specific Homing† | Fold over control phage |
|---------|--------------------------------------|------------------------------------------|------------------|-------------------------|
| LSD | C8161 s.c. xenografts | C8161 xenografts | Yes | 39 |
| | | KRIB xenografts | Yes | 7‡ |
| | | K14-HPV16 skin cancer | No | 5 |
| | | MDA-MB-435 orthotopic xenografts | No | 3 |
| | | MMTV-PyMT breast tumors | No | 3 |
| | | PPC1 orthotopic xenografts | No | 3 |
| | | TRAMP prostate tumors | No | 1 |
| REA | TRAMP prostate tumors | TRAMP prostate tumors | Yes | 46 |
| | | PPC1 orthotopic xenografts | Yes | 25 |
| | | M12 orthotopic xenografts | Yes | 24 |
| | | LNCaP orthotopic xenografts | Yes | 20 |
| | | DU145 orthotopic xenografts | Yes | 14 |
| | | MMTV-PyMT breast tumors | Yes | 8‡ |
| | | K14-HPV16/E$_2$ cervical cancer | Yes | 7‡ |
| | | KRIB xenografts | Yes | 7‡ |
| | | PPC1 s.c. xenografts | No | 6 |
| | | C8161 s.c. xenografts | No | 5 |
| | | K14-HPV16 skin cancer | No | 4 |
| | | MDA-MB-435 orthotopic xenografts | No | 4 |
| AGR | TRAMP PIN lesions | TRAMP PIN lesions | Yes | 18 |
| | | TRAMP prostate tumors | No | 4 |
| | | K14-HPV16/E$_2$ cervical dysplasia | No | 5 |
| | | K14-HPV16/E$_2$ cervical tumors | No | 4 |
| | | MMTV-PyMT premalignant lesions | No | 2 |
| | | MMTV-PyMT breast tumors | No | 4 |

TABLE 3-continued

Main characteristics of lymphatic homing peptides

| Peptide | Tumor used to isolate homing peptide | Tumors tested for phage homing in vivo* | Specific Homing† | Fold over control phage |
|---|---|---|---|---|
| Lyp-2 | K14-HPV16 skin cancer | K14-HPV16/E$_2$ cervical dysplasia | Yes | 17 |
| | | K14-HPV16/E$_2$ cervical tumors | Yes | 22 |
| | | MDA-MB-435 orthotopic xenografts | No | 3 |

*TRAMP, MMTV-PyMT, and K14-HPV16 are genetically engineered mouse models of organ-specific carcinogenesis, each of which presents first with angiogenic dysplasia and subsequently carcinoma.
†The specific homing of phage is considered to be strong (>10-fold compared with control), weak (between 5- and 10-fold), or non-specific (below 5-fold).
‡Phage homing corroborated by fluorescent peptide homing.

The REA phage, which was identified in the TRAMP model, also homed to xenografts obtained by orthotopically inoculating cells from the human prostate cancer cell lines PPC1, M12, DU145, and LNCaP into nude mice (FIG. 5A). These xenografted tumors were also positive with the fluorescein-conjugated REA peptide. In contrast, the MDA-MB-435, C8161, and KRIB xenografts, as well as the de novo breast and skin cancers arising in MMTV-PyMT or K14-HPV16 mice, respectively, were negative for REA binding (FIG. 5A). The cervical tumors of K14-HPV16/E2 mice were slightly positive for REA peptide binding, but markedly less so than the prostate tumors. Immunohistochemical analysis showed that FITC-REA peptide co-localized with lymphatic vessels in orthotopic prostate tumor xenografts arising from multiple human prostate tumor-derived cell lines; this peptide homed to a lesser extent to K14-HPV16/E2 cervical tumors. Interestingly, REA-phage homed less efficiently to subcutaneous xenografts of PPC1 than to orthotopic xenografts of the same tumor cell line (FIG. 10A). The REA-phage strongly bound to PPC1 tumor-derived cell suspensions, but did not bind to cultured PPC1 cells (FIG. 9E). Thus, REA appears to primarily recognize prostate cancer lymphatics.

It was also evaluated whether the REA peptide recognizes human prostate cancers by using phage overlay of tissue sections. Immunohistochemical staining with antibodies against lymphatic markers Prox-1 and podoplanin revealed abundant lymphatic vessels in human prostate tumors. Overlay of tissue sections from two primary human prostate cancers with REA phage indicated that this phage recognizes the lymphatics of human prostate tumors. The AGR phage did not bind to the human tumor sections.

To profile the homing peptide specificity of the AGR peptide in different types of premalignant lesions, three transgenic mouse models were used: TRAMP, K14-HPV16/E2, and MMTV-PyMT, which respectively develop prostate, cervical, or breast neoplasias that subsequently progress to overt cancer. Both AGR phage (FIGS. 2B and 5B) and fluorescent peptide showed marked preference for the TRAMP premalignant lesions; there was little homing of the phage and no detectable homing of the peptide to similar lesions or malignant tumors in the other two models (FIG. 5B).

LyP-1 and LyP-2 have Different Specificities:

Given the similar amino acid sequences of the LyP-1 and LyP-2 peptides, and the fact that they both bind to tumor lymphatics, their specificities were compared. Surprisingly, these peptides recognize different tumors. While both peptides homed to the K14-HPV16 skin cancer lymphatics, LyP-1 phage homed to MDA-MB-435 tumors but not to the cervical tumors, whereas the opposite was true of LyP-2 (FIG. 6). Neither phage homed to the normal cervix or normal breast tissue. To confirm these differences in specificity, peptides were co-injected such that one peptide was a fluorescein conjugate and the other was conjugated to rhodamine, and vice versa. Both LyP-2 conjugates homed to cervical tumors, whereas neither LyP-1 conjugate did so. The opposite result was obtained when the same conjugates were tested in MDA-MB-435 tumor mice. These data indicate that different binding sites exist for the two LyP peptides in different types of tumors.

Identification of a Candidate Homing Peptide Receptor:

Proteins with sequences homologous to the peptides can represent natural ligands for the receptor recognized by the peptide (Joyce et al., 2003). Database searches with the peptides described here revealed some homologies (Table 4), one of which stood out: a homology of the LSD peptide with the chemokine known as stromal cell-derived factor-1 (SDF-1) or CXCL12 (FIG. 7A). CXCL12 is a ligand for the CXCR4 receptor. Transfecting 293T cells with CXCR4 cDNA rendered the cells capable of binding the LSD phage 16-fold more efficiently than mock-transfected cells or cells transfected with VEGFR2 (FIG. 7B). The LyP-1 phage used as a control did not bind to the CXCR4-transfected cells. The cognate LSD peptide inhibited the binding of the LSD phage to the CXCR4-transfected cells in vitro (FIG. 7C). These data indicate that the CXCL12/CXCR4 system is involved in the binding of the LSD peptide to C8161 lymphatics.

TABLE 4

Homing Peptide Homologies

| Peptide | Peptide sequence | Motif | Mouse and human protein with the motif | Accession number |
|---|---|---|---|---|
| LSD | CLSDGKRKC (SEQ ID NO: 4) | C-SDGK (SEQ ID NO: 20) | mSDF-1 | P40224 |
| | | CLSDGK (SEQ ID NO: 2) | hSDF-1 | P48061 |

TABLE 4-continued

Homing Peptide Homologies

| Peptide | Peptide sequence | Motif | Mouse and human protein with the motif | Accession number |
|---------|------------------|-------|----------------------------------------|------------------|
| LDG | CLDGGRPKC (SEQ ID NO: 5) | CLDGG (SEQ ID NO: 21) | unknown | |
| REA | CREAGRKAC (SEQ ID NO: 6) | GRKAC (SEQ ID NO: 22) | hCXCL1 | P09341 |
| | | CREA---AC (SEQ ID NO: 23) | hHGF-like protein precursor | P26927 |
| | | CREAG (SEQ ID NO: 24) | hIL-5R_ chain precursor, CD-MPR | Q01344, P20645 |
| SMS | CSMSAKKKC (SEQ ID NO: 7) | AKKKC (SEQ ID NO: 25) | mIL-17B | Q9QXT6 |
| | | CS-S-KKK (SEQ ID NO: 26) | mSUT-1 | Q9UKG4 |
| | | SMS-KK (SEQ ID NO: 27) | m IL-17Rh1 | Q9JIP3 |
| KTR | CKTRVSCGV (SEQ ID NO: 8) | KTRVS (SEQ ID NO: 28) | hEGF | P01133 |
| AGR | CAGRRSAYC (SEQ ID NO: 9) | CAGRR--S-Y (SEQ ID NO: 29) | hNG3 (VE-statin 2), mNG3 | Q99944, Q6GUQ1 |
| | | RRSAYC (SEQ ID NO: 30) | mType-1B angiotensin IIR | P29755 |
| | | CAGR-SA (SEQ ID NO: 31) | mIL-22R_ chain | Q80XF5 |
| | | RRSAY (SEQ ID NO: 32) | mCD1.2 | P11610 |
| | | RRS-YC (SEQ ID NO: 33) | mLeptin R | P48356 |
| | | CAG-RS-Y (SEQ ID NO: 34) | hIL-27 | Q8TAD2 |
| ASL | CASLSCR (SEQ ID NO: 10) | SLSCR (SEQ ID NO: 35) | mCD28 | P31041 |
| SGG | CSGGKVLDC (SEQ ID NO: 11) | SG-KVLDC (SEQ ID NO: 36) | human integrin alpha-9 | Q13797 |
| | | KVLDC (SEQ ID N0: 37) | Semaphorin receptor SEP | O43157, Q8CJH3 |
| | | C-GG-VLD (SEQ ID NO: 38) | mouse uPAR | P35456 |
| LyP-2 | CNRRTKAGC (SEQ ID NO: 17) | CNRR-K (SEQ ID NO: 39) | Arcadlin | O95206 |
| | | RR-K-GC (SEQ ID NO: 40) | Kinesin-like protein KIF13A | Q9EQW7 |

To identify mouse and human proteins with homologous sequences of peptides, peptides were analyzed by using a NCBI BLAST search against the SWISSPROT database with the option for short nearly exact matches. However, the LSD homology (CLSDGK; SEQ ID NO:2) spans the signal peptide cleavage site of pro-CXCL12 and thus is not represented in the mature chemokine (Nagasawa et al., 1994; Tashiro et al., 1993). Nevertheless, the induction of specific binding capability by transfection of CXCR4 implicates this chemokine receptor, directly or indirectly, as a binding target for the LSD lymphatic homing peptide.

Lymphatic Homing Peptide Conjugates Destroy Tumor Lymphatics:

Conjugates of vascular tumor-homing peptides with the apoptosis-inducing peptide, $_D$(KLAKLAK)$_2$ (SEQ ID NO:19), are selectively cytotoxic to angiogenenic endothelial cells and have demonstrable anti-tumor activity (Ellerby et al., 1999). To determine whether peptides recognizing tumor lymphatics could be used to target those lymphatics, the REA and LSD peptides were synthesized as conjugates with $_D$(KLAKLAK)$_2$ (SEQ ID NO:19) and systemically treated mice bearing PPC1 or C8161 xenografts.

Treatment with the REA conjugate reduced the number of tumor lymphatics in the PPC1 tumors, whereas the uncoupled mixture had no effect compared to the PBS control (FIG. 8A). The conjugate had no effect on tumor blood vessel density (FIG. 8A) or tumor growth (FIG. 8B). Similar reduction of lymphatic vessel density was obtained in C8161 tumor mice treated with the LSD conjugate.

H. References

Arap, W., Pasqualini, R., and Ruoslahti, E. (1998). Chemotherapy targeted to tumor vasculature. Curr Opin Oncol 10, 560-565.

Arbeit, J. M., Howley, P. M., and Hanahan, D. (1996). Chronic estrogen-induced cervical and vaginal squamous carcinogenesis in human papillomavirus type 16 transgenic mice. Proc Natl Acad Sci USA 93, 2930-2935.

Arbeit, J. M., Munger, K., Howley, P. M., and Hanahan, D. (1994). Progressive squamous epithelial neoplasia in K14-human papillomavirus type 16 transgenic mice. J Virol 68, 4358-4368.

Bae, V. L., Jackson-Cook, C. K., Maygarden, S. J., Plymate, S. R., Chen, J., and Ware, J. L. (1998). Metastatic sublines of an SV40 large T antigen immortalized human prostate epithelial cell line. Prostate 34, 275-282.

Borges, E., Jan, Y., and Ruoslahti, E. (2000). Platelet-derived growth factor receptor beta and vascular endothelial growth factor receptor 2 bind to the beta 3 integrin through its extracellular domain. J Biol Chem 275, 39867-39873.

Brooks, P. G., Clouse, J., and Morris, L. S. (1994). Hysterectomy vs. resectoscopic endometrial ablation for the control of abnormal uterine bleeding. A cost-comparative study. J Reprod Med 39, 755-760.

Cao, R., Bjorndahl, M. A., Religa, P., Clasper, S., Garvin, S., Galter, D., Meister, B., Ikomi, F., Tritsaris, K., Dissing, S., et al. (2004). PDGF-BB induces intratumoral lymphangiogenesis and promotes lymphatic metastasis. Cancer Cell 6, 333-345.

Cassella, M., and Skobe, M. (2002). Lymphatic vessel activation in cancer. Ann N Y Acad Sci 979, 120-130.

Christian, S., Pilch, J., Akerman, M. E., Porkka, K., Laakkonen, P., and Ruoslahti, E. (2003). Nucleolin expressed at the cell surface is a marker of endothelial cells in angiogenic blood vessels. J Cell Biol 163, 871-878.

Coussens, L. M., Hanahan, D., and Arbeit, J. M. (1996). Genetic predisposition and parameters of malignant progression in K14-HPV16 transgenic mice. Am J Pathol 149, 1899-1917.

Curnis, F., Gasparri, A., Sacchi, A., Longhi, R., and Corti, A. (2004). Coupling tumor necrosis factor-alpha with alphaV integrin ligands improves its antineoplastic activity. Cancer Res 64, 565-571.

Curnis, F., Sacchi, A., Borgna, L., Magni, F., Gasparri, A., and Corti, A. (2000). Enhancement of tumor necrosis factor alpha antitumor immunotherapeutic properties by targeted delivery to aminopeptidase N (CD13). Nat Biotechnol 18, 1185-1190.

Ellerby, H. M., Arap, W., Ellerby, L. M., Kain, R., Andrusiak, R., Rio, G. D., Krajewski, S., Lombardo, C. R., Rao, R., Ruoslahti, E., et al. (1999). Anti-cancer activity of targeted pro-apoptotic peptides. Nat Med 5, 1032-1038.

Ferrara, N., and Alitalo, K. (1999). Clinical applications of angiogenic growth factors and their inhibitors. Nat Med 5, 1359-1364.

Giraudo, E., Inoue, M., and Hanahan, D. (2004). An aminobisphosphonate targets MMP-9-expressing macrophages and angiogenesis to impair cervical carcinogenesis. J Clin Invest 114, 623-633.

Hanahan, D., and Weinberg, R. A. (2000). The hallmarks of cancer. Cell 100, 57-70.

Helbig, G., Christopherson, K. W., 2nd, Bhat-Nakshatri, P., Kumar, S., Kishimoto, H., Miller, K. D., Broxmeyer, H. E., and Nakshatri, H. (2003). NF-kappaB promotes breast cancer cell migration and metastasis by inducing the expression of the chemokine receptor CXCR4. J Biol Chem 278, 21631-21638.

Hoffman, J., Laakkonen, P., Porkka, K., Bernasconi, M., and Ruoslahti, E (2004). In vivo and ex vivo selections using phage-displayed libraries.

Hoffman, J. A., Giraudo, E., Singh, M., Zhang, L., Inoue, M., Porkka, K., Hanahan, D., and Ruoslahti, E. (2003). Progressive vascular changes in a transgenic mouse model of squamous cell carcinoma. Cancer Cell 4, 383-391.

Hsu, C. X., Ross, B. D., Chrisp, C. E., Derrow, S. Z., Charles, L. G., Pienta, K. J., Greenberg, N. M., Zeng, Z., and Sanda, M. G. (1998). Longitudinal cohort analysis of lethal prostate cancer progression in transgenic mice. J Urol 160, 1500-1505.

Jackson, D. G., Prevo, R., Clasper, S., and Banerji, S. (2001). LYVE-1, the lymphatic system and tumor lymphangiogenesis. Trends Immunol 22, 317-321.

Joyce, J. A., Laakkonen, P., Bernasconi, M., Bergers, G., Ruoslahti, E., and Hanahan, D. (2003). Stage-specific vascular markers revealed by phage display in a mouse model of pancreatic islet tumorigenesis. Cancer Cell 4, 393-403.

Laakkonen, P., Akerman, M. E., Biliran, H., Yang, M., Ferrer, F., Karpanen, T., Hoffman, R. M., and Ruoslahti, E. (2004). Antitumor activity of a homing peptide that targets tumor lymphatics and tumor cells. Proc Natl Acad Sci USA 101, 9381-9386.

Laakkonen, P., Porkka, K., Hoffman, J. A., and Ruoslahti, E. (2002). A tumor-homing peptide with a targeting specificity related to lymphatic vessels. Nat Med 8, 751-755.

Lin, J., Lalani, A. S., Harding, T. C., Gonzalez, M., Wu, W. W., Luan, B., Tu, G. H., Koprivnikar, K., VanRoey, M. J., He, Y., et al. (2005). Inhibition of lymphogenous metastasis using adeno-associated virus-mediated gene transfer of a soluble VEGFR-3 decoy receptor. Cancer Res 65, 6901-6909.

Mandriota, S. J., Jussila, L., Jeltsch, M., Compagni, A., Baetens, D., Prevo, R., Banerji, S., Huarte, J., Montesano, R., Jackson, D. G., et al. (2001). Vascular endothelial growth factor-C-mediated lymphangiogenesis promotes tumour metastasis. Embo J 20, 672-682.

Mouta Carreira, C., Nasser, S. M., di Tomaso, E., Padera, T. P., Boucher, Y., Tomarev, S. I., and Jain, R. K. (2001). LYVE-1 is not restricted to the lymph vessels: expression in normal liver blood sinusoids and down-regulation in human liver cancer and cirrhosis. Cancer Res 61, 8079-8084.

Nagasawa, T., Kikutani, H., and Kishimoto, T. (1994). Molecular cloning and structure of a pre-B-cell growth-stimulating factor. Proc Natl Acad Sci USA 91, 2305-2309.

Padera, T. P., Kadambi, A., di Tomaso, E., Carreira, C. M., Brown, E. B., Boucher, Y., Choi, N. C., Mathisen, D., Wain, J., Mark, E. J., et al. (2002). Lymphatic metastasis in the absence of functional intratumor lymphatics. Science 296, 1883-1886.

Pasqualini, R., Koivunen, E., Kain, R., Landenranta, J., Sakamoto, M., Stryhn, A., Ashmun, R. A., Shapiro, L. H., Arap, W., and Ruoslahti, E. (2000). Aminopeptidase N is a receptor for tumor-homing peptides and a target for inhibiting angiogenesis. Cancer Res 60, 722-727.

Ruoslahti, E. (2002). Specialization of tumour vasculature. Nat Rev Cancer 2, 83-90.

Ruoslahti, E. (2003). The RGD story: a personal account. Matrix Biol 22, 459-465.

Saharinen, P., Tammela, T., Karkkainen, M. J., and Alitalo, K. (2004). Lymphatic vasculature: development, molecular regulation and role in tumor metastasis and inflammation. Trends Immunol 25, 387-395.

Skobe, M., Hawighorst, T., Jackson, D. G., Prevo, R., Janes, L., Velasco, P., Riccardi, L., Alitalo, K., Claffey, K., and Detmar, M. (2001). Induction of tumor lymphangiogenesis by VEGF-C promotes breast cancer metastasis. Nat Med 7, 192-198.

Stacker, S. A., Achen, M. G., Jussila, L., Baldwin, M. E., and Alitalo, K. (2002). Lymphangiogenesis and cancer metastasis. Nat Rev Cancer 2, 573-583.

Stacker, S. A., Caesar, C., Baldwin, M. E., Thornton, G. E., Williams, R. A., Prevo, R., Jackson, D. G., Nishikawa, S., Kubo, H., and Achen, M. G. (2001). VEGF-D promotes the metastatic spread of tumor cells via the lymphatics. Nat Med 7, 186-191.

Tashiro, K., Tada, H., Heilker, R., Shirozu, M., Nakano, T., and Honjo, T. (1993). Signal sequence trap: a cloning strategy for secreted proteins and type I membrane proteins. Science 261, 600-603.

Valtola, R., Salven, P., Heikkila, P., Taipale, J., Joensuu, H., Rehn, M., Pihlajaniemi, T., Weich, H., deWaal, R., and Alitalo, K. (1999). VEGFR-3 and its ligand VEGF-C are associated with angiogenesis in breast cancer. Am J Pathol 154, 1381-1390.

Yao, V. J., Ozawa, M. G., Trepel, M., Arap, W., McDonald, D. M., and Pasqualini, R. (2005). Targeting pancreatic islets with phage display assisted by laser pressure catapult microdissection. Am J Pathol 166, 625-636.

| I. | Sequences |
|---|---|
| 1. | SEQ ID NO: 1-hSDF-1<br>MNAKVVVVLVLVLTALCLSDGKPVS |
| 2. | SEQ ID NO: 2<br>CLSDGK |
| 3. | SEQ ID NO: 3<br>CLSDGKPVS |
| 4. | SEQ ID NO: 4-LSD<br>CLSDGKRKC |
| 5. | SEQ ID NO: 5-LDG<br>CLDGGRPKC |
| 6. | SEQ ID NO: 6-REA<br>CREAGRKAC |
| 7. | SEQ ID NO: 7-SMS<br>CSMSAKKKC |
| 8. | SEQ ID NO: 8-KTR<br>CKTRVSCGV |
| 9. | SEQ ID NO: 9-AGR<br>CAGRRSAYC |
| 10. | SEQ ID NO: 10-ASL<br>CASLSCR |
| 11. | SEQ ID NO: 11-SGG<br>CSGGKVLDC |
| 12. | SEQ ID NO: 12<br>KRTR |
| 13. | SEQ ID NO: 13<br>RRTR |
| 14. | SEQ ID NO: 14<br>KRTK |
| 15. | SEQ ID NO: 15<br>RRTK |
| 16. | SEQ ID NO: 16-LyP-1<br>CGNKRTRGC |
| 17. | SEQ ID NO: 17-LyP-2<br>CNRRTKAGC |
| 18. | SEQ ID NO 18-LyP-3<br>CNKRTRGGC |

-continued

| I. | Sequences |
|---|---|
| 19. | SEQ ID NO: 19<br>$_D$KLAKLAKKLAKLAK |
| 20. | SEQ ID NO: 20<br>C-SDGK |
| 21. | SEQ ID NO: 21<br>CLDGG |
| 22. | SEQ ID NO: 22<br>GRKAC |
| 23. | SEQ ID NO: 23<br>CREA---AC |
| 24. | SEQ ID NO: 24<br>CREAG |
| 25. | SEQ ID NO: 25<br>AKKKC |
| 26. | SEQ ID NO: 26<br>CS-S-KKK |
| 27. | SEQ ID NO: 27<br>SMS-KK |
| 28. | SEQ ID NO: 28<br>KTRVS |
| 29. | SEQ ID NO: 29<br>CAGRR--S-Y |
| 30. | SEQ ID NO: 30<br>RRSAYC |
| 31. | SEQ ID NO: 31<br>CAGR-SA |
| 32. | SEQ ID NO: 32<br>RRSAY |
| 33. | SEQ ID NO: 33<br>RRS-YC |
| 34. | SEQ ID NO: 34<br>CAG-RS-Y |
| 35. | SEQ ID NO: 35<br>SLSCR |
| 36. | SEQ ID NO: 36<br>SG-KVLDC |
| 37. | SEQ ID NO: 37<br>KVLDC |
| 38. | SEQ ID NO: 38<br>C-GG-VLD |
| 39. | SEQ ID NO: 39<br>CNRR-K |
| 40. | SEQ ID NO: 40<br>RR-K-GC |
| 41. | SEQ ID NO: 41<br>$_D$KLAKLAKKLAKLAK-CREAGRKAC |
| 42. | SEQ ID NO: 42<br>$_D$KLAKLAKKLAKLAK-CLSDCGKRKC |
| 43. | SEQ ID NO: 43-mSDF-1<br>MDAKVVAVLALVLAALCISDGKPVS |
| 44. | SEQ ID NO: 44-Antp<br>RQPKIWFPNRRKPWKK |

| I. | Sequences |
|---|---|
| 45. | SEQ ID NO: 45-HIV-Tat<br>GRKKRRQRPPQ |
| 46. | SEQ ID NO: 46-Penetratin<br>RQIKIWFQNRRMKWKK |
| 47. | SEQ ID NO: 47-Antp-3A<br>RQIAIWFQNRRMKWAA |
| 48. | SEQ ID NO: 48-Tat<br>RKKRRQRRR |
| 49. | SEQ ID NO: 49-Buforin II<br>TRSSRAGLQFPVGRVHRLLRK |
| 50. | SEQ ID NO: 50-Transportan<br>GWTLNSAGYLLGKINKALAALAKKIL |
| 51. | SEQ ID NO: 51-model amphipathic peptide (MAP)<br>KLALKLALKALKAALKLA |
| 52. | SEQ ID NO: 52-K-FGF<br>AAVALLPAVLLALLAP |
| 53. | SEQ ID NO: 53-Ku70<br>VPMLK-PMLKE |
| 54. | SEQ ID NO: 54-Prion<br>MANLGYWLLALFVTMWTDVGLCKKRPKP |
| 55. | SEQ ID NO: 55-pVEC<br>LLIILRRRIRKQAHAHSK |
| 56. | SEQ ID NO: 56-Pep-1<br>KETWWETWWTEWSQPKKKRKV |
| 57. | SEQ ID NO: 57-SynB1<br>RGGRLSYSRRRFSTSTGR |
| 58. | SEQ ID NO: 58-Pep-7<br>SDLWEMMMVSLACQY |
| 59. | SEQ ID NO: 59-HN-1<br>TSPLNIHNGQKL |
| 60. | SEQ ID NO: 60<br>XRTX, where X is R or T |

The invention claimed is:

1. An isolated peptide having a length of up to 50 amino acids comprising
CREAGRKAC (SEQ ID NO:6),
wherein the peptide selectively binds to tumor lymphatics.

2. The peptide of claim 1, wherein the peptide has a length of up to 25 amino acids.

3. The peptide of claim 2, wherein the peptide has a length of from 9 to 25 amino acids.

4. A conjugate comprising the peptide of claim 1 conjugated to a moiety, wherein the conjugate selectively homes to tumor lymphatics.

5. A conjugate comprising the peptide of claim 1 and a moiety selected from the group consisting of a therapeutic moiety, a detectable moiety, a cytotoxic agent, an anti-lymphangiogenic agent, a cancer chemotherapeutic agent, a pro-apoptotic polypeptide, a grafted polypeptide, a virus, a cell, and a liposome, wherein the conjugate selectively homes to tumor lymphatics.

6. The conjugate of claim 5, wherein the moiety is a cytotoxic agent, wherein the cytotoxic agent is $_D$(KLAKLAK)$_2$ (SEQ ID NO:19).

7. The conjugate of claim 5, wherein the moiety is a detection moiety selected from a fluorophore, enzyme, biotin, metal, or epitope tag.

8. A method of detecting cancer in a subject, comprising administering to the subject the conjugate of claim 5 and detecting the presence of the conjugate in the lymphatics of the subject, wherein detecting the presence of more of the conjugate in the lymphatics than a reference or control amount indicates the presence of cancer.

9. A method of detecting cancer, comprising contacting a biological sample with the conjugate of claim 5 and detecting the presence of the conjugate in the lymphatics of the sample, wherein detecting the presence of more of the conjugate in the lymphatics than a reference or control amount indicates the presence of cancer.

10. A method of treating prostate cancer in a subject, comprising administering to the subject the conjugate of claim 5, wherein the conjugate inhibits lymphangiogenesis in a tumor in the subject.

11. The method of claim 10, wherein the prostate cancer is malignant prostate cancer.

12. A method of determining malignant prostate conditions in a subject, comprising contacting a biological sample from the subject with a conjugate according to claim 4.

13. An isolated nucleic acid encoding the polypeptide of claim 1.

14. The isolated nucleic acid of claim 13 further comprising a nucleic acid encoding a internalization sequence.

15. The isolated nucleic acid of claim 14, wherein the cellular internalization comprises an amino acid sequence of a protein selected from a group consisting of Antennapedia, TAT, HIV-Tat, Penetratin, Antp-3A (Antp mutant), Buforin II, Transportan, MAP (model amphipathic peptide), K-FGF, Ku70, Prion, pVEC, Pep-1, SynB1, Pep-7, HN-1, BGSC (Bis-Guanidinium-Spermidine-Cholesterol and BGTC (Bis-Guanidinium-Tren-Cholesterol.

16. An expression vector comprising an isolated nucleic acid of claim 14, wherein the nucleic acid is operably linked to an expression control sequence.

* * * * *

SEQUENCE LISTING

```
<160> NUMBER OF SEQ ID NOS: 60

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 1

Met Asn Ala Lys Val Val Val Leu Val Leu Val Leu Thr Ala Leu
1               5                   10                  15

Cys Leu Ser Asp Gly Lys Pro Val Ser
            20                  25

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 2

Cys Leu Ser Asp Gly Lys
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 3

Cys Leu Ser Asp Gly Lys Pro Val Ser
1               5
```

```
<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 4

Cys Leu Ser Asp Gly Lys Arg Lys Cys
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 5

Cys Leu Asp Gly Gly Arg Pro Lys Cys
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 6

Cys Arg Glu Ala Gly Arg Lys Ala Cys
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 7

Cys Ser Met Ser Ala Lys Lys Lys Cys
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 8

Cys Lys Thr Arg Val Ser Cys Gly Val
1               5

<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct
```

```
<400> SEQUENCE: 9

Cys Ala Gly Arg Arg Ser Ala Tyr Cys
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 10

Cys Ala Ser Leu Ser Cys Arg
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 11

Cys Ser Gly Gly Lys Val Leu Asp Cys
1               5

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 12

Lys Arg Thr Arg
1

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 13

Arg Arg Thr Arg
1

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 14

Lys Arg Thr Lys
1

<210> SEQ ID NO 15
<211> LENGTH: 4
<212> TYPE: PRT
<213> ORGANISM: Artificial Sequence
```

```
<220> FEATURE:
<223> OTHER INFORMATION: Description of Artificial Sequence: note =
      synthetic construct

<400> SEQUENCE: 15

Arg Arg Thr Lys
1

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 16

Cys Gly Asn Lys Arg Thr Arg Gly Cys
1               5

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 17

Cys Asn Arg Arg Thr Lys Ala Gly Cys
1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 18

Cys Asn Lys Arg Thr Arg Gly Gly Cys
1               5

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 19

Lys Leu Ala Lys Leu Ala Lys Lys Leu Ala Lys Leu Ala Lys
1               5                   10

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: MISC_FEATURE
<222> LOCATION: (2)..(2)
<223> OTHER INFORMATION: X can be any amino acid

<400> SEQUENCE: 20
```

```
Cys Xaa Ser Asp Gly Lys
1               5

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 21

Cys Leu Asp Gly Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 22

Gly Arg Lys Ala Cys
1               5

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: VARIANT
<222> LOCATION: (5)..(7)
<223> OTHER INFORMATION: Xaa = any amino acid

<400> SEQUENCE: 23

Cys Arg Glu Ala Xaa Xaa Xaa Ala Cys
1               5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 24

Cys Arg Glu Ala Gly
1               5

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 25

Ala Lys Lys Lys Cys
1               5

<210> SEQ ID NO 26
<211> LENGTH: 8
```

```
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: MISC_FEATURE
<222> LOCATION: (3)..(3)
<220> FEATURE:
<221> NAME/KEY: MISC_FEATURE
<222> LOCATION: (5)..(5)

<400> SEQUENCE: 26

Cys Ser Xaa Ser Xaa Lys Lys Lys
1               5

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: MISC_FEATURE
<222> LOCATION: (4)..(4)
<223> OTHER INFORMATION: X can be any amino acid

<400> SEQUENCE: 27

Ser Met Ser Xaa Lys Lys
1               5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 28

Lys Thr Arg Val Ser
1               5

<210> SEQ ID NO 29
<211> LENGTH: 10
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: VARIANT
<222> LOCATION: (6)..(7)
<223> OTHER INFORMATION: Xaa = any amino acid
<220> FEATURE:
<221> NAME/KEY: VARIANT
<222> LOCATION: (9)..(9)
<223> OTHER INFORMATION: Xaa = any amino acid

<400> SEQUENCE: 29

Cys Ala Gly Arg Arg Xaa Xaa Ser Xaa Tyr
1               5                   10

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: note =
      synthetic construct
```

```
<400> SEQUENCE: 30

Arg Arg Ser Ala Tyr Cys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: MISC_FEATURE
<222> LOCATION: (5)..(5)
<223> OTHER INFORMATION: X can be any amino acid

<400> SEQUENCE: 31

Cys Ala Gly Arg Xaa Ser Ala
1               5

<210> SEQ ID NO 32
<211> LENGTH: 5
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 32

Arg Arg Ser Ala Tyr
1               5

<210> SEQ ID NO 33
<211> LENGTH: 6
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: MISC_FEATURE
<222> LOCATION: (4)..(4)
<223> OTHER INFORMATION: X can be any amino acid

<400> SEQUENCE: 33

Arg Arg Ser Xaa Tyr Cys
1               5

<210> SEQ ID NO 34
<211> LENGTH: 8
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: MISC_FEATURE
<222> LOCATION: (4)..(4)
<223> OTHER INFORMATION: X can be any amino acid
<220> FEATURE:
<221> NAME/KEY: MISC_FEATURE
<222> LOCATION: (7)..(7)
<223> OTHER INFORMATION: X can be any amino acid

<400> SEQUENCE: 34

Cys Ala Gly Xaa Arg Ser Xaa Tyr
1               5

<210> SEQ ID NO 35
<211> LENGTH: 5
```

```
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 35

Ser Leu Ser Cys Arg
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: MISC_FEATURE
<222> LOCATION: (3)..(3)
<223> OTHER INFORMATION: X can be any amino acid

<400> SEQUENCE: 36

Ser Gly Xaa Lys Val Leu Asp Cys
1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 37

Lys Val Leu Asp Cys
1               5

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: MISC_FEATURE
<222> LOCATION: (2)..(2)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid

<400> SEQUENCE: 38

Cys Xaa Gly Gly Xaa Val Leu Asp
1               5

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: MISC_FEATURE
<222> LOCATION: (5)..(5)
<223> OTHER INFORMATION: X can be any amino acid

<400> SEQUENCE: 39
```

```
Cys Asn Arg Arg Xaa Lys
1               5

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: MISC_FEATURE
<222> LOCATION: (3)..(3)
<223> OTHER INFORMATION: X can be any amino acid
<220> FEATURE:
<221> NAME/KEY: MISC_FEATURE
<222> LOCATION: (5)..(5)
<223> OTHER INFORMATION: X can be any amino acid

<400> SEQUENCE: 40

Arg Arg Xaa Lys Xaa Gly Cys
1               5

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 41

Lys Leu Ala Lys Leu Ala Lys Lys Leu Ala Lys Leu Ala Lys Cys Arg
1               5                   10                  15

Glu Ala Gly Arg Lys Ala Cys
            20

<210> SEQ ID NO 42
<211> LENGTH: 24
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 42

Lys Leu Ala Lys Leu Ala Lys Lys Leu Ala Lys Leu Ala Lys Cys Leu
1               5                   10                  15

Ser Asp Cys Gly Lys Arg Lys Cys
            20

<210> SEQ ID NO 43
<211> LENGTH: 25
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 43

Met Asp Ala Lys Val Val Ala Val Leu Ala Leu Val Leu Ala Ala Leu
1               5                   10                  15

Cys Ile Ser Asp Gly Lys Pro Val Ser
            20                  25

<210> SEQ ID NO 44
<211> LENGTH: 16
<212> TYPE: PRT
```

```
<213> ORGANISM: Artificial Sequence
<220> FEATURE:
<223> OTHER INFORMATION: Description of Artificial Sequence: note =
      synthetic construct

<400> SEQUENCE: 44

Arg Gln Pro Lys Ile Trp Phe Pro Asn Arg Arg Lys Pro Trp Lys Lys
1               5                   10                  15

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 45

Gly Arg Lys Lys Arg Arg Gln Arg Pro Pro Gln
1               5                   10

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 46

Arg Gln Ile Lys Ile Trp Phe Gln Asn Arg Arg Met Lys Trp Lys Lys
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 47

Arg Gln Ile Ala Ile Trp Phe Gln Asn Arg Arg Met Lys Trp Ala Ala
1               5                   10                  15

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 48

Arg Lys Lys Arg Arg Gln Arg Arg Arg
1               5

<210> SEQ ID NO 49
<211> LENGTH: 21
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 49

Thr Arg Ser Ser Arg Ala Gly Leu Gln Phe Pro Val Gly Arg Val His
1               5                   10                  15
```

Arg Leu Leu Arg Lys
            20

<210> SEQ ID NO 50
<211> LENGTH: 26
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 50

Gly Trp Thr Leu Asn Ser Ala Gly Tyr Leu Leu Gly Lys Ile Asn Lys
1               5                   10                  15

Ala Leu Ala Ala Leu Ala Lys Lys Ile Leu
            20                  25

<210> SEQ ID NO 51
<211> LENGTH: 18
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 51

Lys Leu Ala Leu Lys Leu Ala Leu Lys Ala Leu Lys Ala Ala Leu Lys
1               5                   10                  15

Leu Ala

<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 52

Ala Ala Val Ala Leu Leu Pro Ala Val Leu Leu Ala Leu Leu Ala Pro
1               5                   10                  15

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 53

Val Pro Met Leu Lys Pro Met Leu Lys Glu
1               5                   10

<210> SEQ ID NO 54
<211> LENGTH: 28
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 54

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro
            20                  25

```
<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 55

Leu Leu Ile Ile Leu Arg Arg Arg Ile Arg Lys Gln Ala His Ala His
1               5                   10                  15

Ser Lys

<210> SEQ ID NO 56
<211> LENGTH: 21
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 56

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 57
<211> LENGTH: 18
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 57

Arg Gly Gly Arg Leu Ser Tyr Ser Arg Arg Arg Phe Ser Thr Ser Thr
1               5                   10                  15

Gly Arg

<210> SEQ ID NO 58
<211> LENGTH: 15
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 58

Ser Asp Leu Trp Glu Met Met Met Val Ser Leu Ala Cys Gln Tyr
1               5                   10                  15

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: note =
      synthetic construct

<400> SEQUENCE: 59

Thr Ser Pro Leu Asn Ile His Asn Gly Gln Lys Leu
1               5                   10

<210> SEQ ID NO 60
```

```
<211> LENGTH: 4
<212> TYPE: PRT
<213> ORGANISM: Artificial Sequence
<220> FEATURE:
<223> OTHER INFORMATION: Description of Artificial Sequence: note =
      synthetic construct
<220> FEATURE:
<221> NAME/KEY: VARIANT
<222> LOCATION: (1)..(4)
<223> OTHER INFORMATION: Xaa at positions 1 and 4 can be any amino acid

<400> SEQUENCE: 60

Xaa Arg Thr Xaa
1
```